US012312600B2

(12) United States Patent
Thurner et al.

(10) Patent No.: US 12,312,600 B2
(45) Date of Patent: May 27, 2025

(54) METHODS FOR OBTAINING INDUCED SMOOTH MUSCLE CELLS

(71) Applicant: INNOVACELL GMBH, Innsbruck (AT)

(72) Inventors: Marco Thurner, Innsbruck (AT); Rainer Marksteiner, Schwaz (AT)

(73) Assignee: INNOVACELL GMBH, Innsbruck (AT)

( * ) Notice: Subject to any disclaimer, the term of this patent is extended or adjusted under 35 U.S.C. 154(b) by 102 days.

(21) Appl. No.: 17/441,690

(22) PCT Filed: Mar. 23, 2020

(86) PCT No.: PCT/EP2020/057940
§ 371 (c)(1),
(2) Date: Sep. 21, 2021

(87) PCT Pub. No.: WO2020/193460
PCT Pub. Date: Oct. 1, 2020

(65) Prior Publication Data
US 2022/0145257 A1    May 12, 2022

(30) Foreign Application Priority Data
Mar. 22, 2019  (EP) ..................... 19164574

(51) Int. Cl.
*C12N 5/077*     (2010.01)
*A61K 35/34*     (2015.01)

(52) U.S. Cl.
CPC ............ *C12N 5/0661* (2013.01); *A61K 35/34* (2013.01); *C12N 2501/15* (2013.01); *C12N 2501/91* (2013.01); *C12N 2506/1323* (2013.01); *C12N 2513/00* (2013.01)

(58) Field of Classification Search
CPC ........ C12N 5/0661; A61K 35/34; A61P 21/00
USPC ...................................... 424/93.21
See application file for complete search history.

(56) References Cited

U.S. PATENT DOCUMENTS

| 5,667,778 | A  | * | 9/1997  | Atala ............. A61L 27/50 424/423 |
|---|---|---|---|---|
| 2005/0079606 | A1 |   | 4/2005  | Tamaki et al. |
| 2007/0264712 | A1 |   | 11/2007 | Savant-Bhonsale |
| 2008/0213231 | A1 |   | 9/2008  | Oh et al. |
| 2009/0010897 | A1 |   | 1/2009  | Chancellor et al. |
| 2009/0155221 | A1 |   | 6/2009  | Payne et al. |
| 2009/0269310 | A1 |   | 10/2009 | Le Ricousse et al. |
| 2021/0069255 | A1 |   | 3/2021  | Thurner et al. |
| 2022/0145257 | A1 |   | 5/2022  | Thurner et al. |
| 2023/0285467 | A1 |   | 9/2023  | Turner et al. |

FOREIGN PATENT DOCUMENTS

| CN | 101310013 A | 11/2008 | |
|---|---|---|---|
| CN | 103230415 A | 8/2013 | |
| CN | 106350480 A | 1/2017 | |
| EP | 2120976 B1 | 11/2009 | |
| EP | 2 206 774 | 7/2010 | |
| EP | 3056562 A1 * | 8/2016 | ........... C12N 5/0691 |
| JP | 2009-508511 A | 3/2009 | |
| WO | WO 01/78754 | 10/2001 | |
| WO | WO 03/027281 | 4/2003 | |
| WO | WO 2007/010858 A1 | 1/2007 | |
| WO | WO 2007/106200 | 9/2007 | |
| WO | WO 2008/153813 | 12/2008 | |
| WO | WO 2014/044867 | 3/2014 | |
| WO | WO 2019/115790 A1 | 6/2019 | |
| WO | WO 2020/193460 | 10/2020 | |
| WO | WO 2023/012334 A1 | 2/2023 | |

OTHER PUBLICATIONS

Shudo et al., "Isolation and trans-differentiation of mesenchymal stromal cells into smooth muscle cells: Utility and applicability for cell-sheet engineering". Cytotherapy. Apr. 2016; 18(4): 510-517. (Year: 2016).*
Park et al., "Functional expression of smooth muscle-specific ion channels in TGF-β-treated human adipose-derived mesenchymal stem cells". Am J Physiol Cell Physiol. 2013;305(4):1-12. (Year: 2013).*
Gong et al., "Influence of Culture Medium on Smooth Muscle Cell Differentiation from Human Bone Marrow-Derived Mesenchymal Stem Cells". Tissue Eng Part A. Feb. 2009;15(2):319-330 (Year: 2009).*
Villiers et al. (Villiers et al., "Adipose Derived Stem Cells and Smooth Muscle Cells: Implications for Regenerative Medicine". Stem Cell Rev and Rep 5, pp. 256-265 (Year: 2009).*
Sandison et al., "Heterogeneity in the Proliferative Capacity of Smooth Muscle Cells (SMCs)". FASEB; 29(1): 1-2 (Year: 2015).*
Orlandi et al., "Proliferative Activity and a-Smooth Muscle Actin Expression in Cultured Rat Aortic Smooth Muscle Cells Are Differently Modulated by Transforming Growth Factor-β1 and Heparin". Experimental Cell Research. vol. 214, Issue 2, 1994. pp. 528-536 (Year: 1994).*
Abrahamsson, Hasse. "Treatment options for patients with severe gastroparesis." Gut 56.6 (2007): 877-883.
Abujarour, Ramzey, et al. "Myogenic differentiation of muscular dystrophy-specific induced pluripotent stem cells for use in drug discovery." *Stem cells translational medicine* 3.2 (2014): 149-160.
Al-Ali, S., et al. "Correlation between gross anatomical topography, sectional sheet plastination, microscopic anatomy and endoanal sonography of the anal sphincter complex in human males." *Journal of Anatomy* 215.2 (2009): 212-220.
Bajpai, Vivek K., et al. "Functional vascular smooth muscle cells derived from human induced pluripotent stem cells via mesenchymal stem cell intermediates." *Cardiovascular research* 96.3 (2012): 391-400.

(Continued)

*Primary Examiner* — Allison M Fox
*Assistant Examiner* — Hanan Isam Abuzeineh
(74) *Attorney, Agent, or Firm* — Parker Highlander PLLC

(57) ABSTRACT

The present invention relates to methods for obtaining induced smooth muscle cells (iSMCs), iSMCs, iSMCs for use in a method of treating a disease or disorder or for use in tissue engineering, and the use of skeletal muscle derived cells for obtaining iSMCs.

7 Claims, 15 Drawing Sheets

(56) References Cited

OTHER PUBLICATIONS

Belkin, Vladimir M., Alexey M. Belkin, and Victor E. Koteliansky. "Human smooth muscle VLA-1 integrin: purification, substrate specificity, localization in aorta, and expression during development." *The Journal of cell biology* 111.5 (1990): 2159-2170.

Bohl, Jaime L., Elie Zakhem, and Khalil N. Bitar. "Successful treatment of passive fecal incontinence in an animal model using engineered biosphincters: a 3-month follow-up study." *Stem cells translational medicine* 6.9 (2017): 1795-1802.

Capetanaki, Yassemi, Derek J. Milner, and G. Weitzer. "Desmin in muscle formation and maintenance: knockouts and consequences." *Cell structure and function* 22.1 (1997): 103-116.

Dash, Biraja C., et al. "Tissue-engineered vascular rings from human iPSC-derived smooth muscle cells." *Stem Cell Reports* 7.1 (2016): 19-28.

Dominici, M et al. "Minimal criteria for defining multipotent mesenchymal stromal cells. The International Society for Cellular Therapy position statement." *Cytotherapy* vol. 8,4 (2006): 315-7.

Espagnolle, Nicolas et al. "CD146 expression on mesenchymal stem cells is associated with their vascular smooth muscle commitment." *Journal of cellular and molecular medicine* vol. 18,1 (2014): 104-14.

Freshney, R. Ian. "Primary Culture." In: *Culture of animal cells: a manual of basic technique and specialized applications*. John Wiley & Sons, 2010. pp. 163-186.

Frudinger, A et al. "Autologous skeletal-muscle-derived cell injection for anal incontinence due to obstetric trauma: a 5-year follow-up of an initial study of 10 patients." *Colorectal disease : the official journal of the Association of Coloproctology of Great Britain and Ireland* vol. 17,9 (2015): 794-801.

Frudinger, A et al. "Muscle-derived cell injection to treat anal incontinence due to obstetric trauma: pilot study with 1 year follow-up." *Gut* vol. 59,1 (2010): 55-61.

Frudinger, Andrea et al. "Skeletal muscle-derived cell implantation for the treatment of sphincter-related faecal incontinence." *Stem cell research & therapy* vol. 9,1 233. Sep. 13, 2018.

Gharaibeh, Burhan, et al. "Isolation of a slowly adhering cell fraction containing stem cells from murine skeletal muscle by the preplate technique." *Nature protocols* 3.9 (2008): 1501.

Goode, Patricia S et al. "Prevalence and correlates of fecal incontinence in community-dwelling older adults." *Journal of the American Geriatrics Society* vol. 53,4 (2005): 629-35.

Huard, J et al. "Muscle-derived cell-mediated ex vivo gene therapy for urological dysfunction." *Gene therapy* vol. 9,23 (2002): 1617-26.

Iivanainen, A et al. "Primary structure and expression of a novel human laminin α4 chain." *FEBS letters* vol. 365,2-3 (1995): 183-8.

International Search Report and Written Opinion issued in International Application No. PCT/EP2018/085015, mailed Feb. 18, 2019.

International Search Report and Written Opinion issued in International Application No. PCT/EP2020/057940, mailed Apr. 22, 2020.

Jung, Yunjoon et al. "Concise review: Induced pluripotent stem cell-derived mesenchymal stem cells: progress toward safe clinical products." *Stem cells (Dayton, Ohio)* vol. 30,1 (2012): 42-7.

Krauss, Robert S et al. "Embracing change: striated-for-smooth muscle replacement in esophagus development." *Skeletal muscle* vol. 6 27. Aug. 8, 2016.

Lecourt, Séverine et al. "Characterization of distinct mesenchymal-like cell populations from human skeletal muscle in situ and in vitro." *Experimental cell research* vol. 316,15 (2010): 2513-26.

Li, Yanhui et al. "Smooth Muscle Progenitor Cells Derived From Human Pluripotent Stem Cells Induce Histologic Changes in Injured Urethral Sphincter." *Stem cells translational medicine* vol. 5,12 (2016): 1719-1729.

Lu, A., et al. "Isolation of myogenic progenitor populations from Pax7-deficient skeletal muscle based on adhesion characteristics." *Gene therapy* 15.15 (2008): 1116-1125.

Lu, Shing-Hwa et al. "Characterization of smooth muscle differentiation of purified human skeletal muscle-derived cells." *Journal of cellular and molecular medicine* vol. 15,3 (2011): 587-92.

McHugh, K M. "Molecular analysis of smooth muscle development in the mouse." *Developmental dynamics: an official publication of the American Association of Anatomists* vol. 204,3 (1995): 278-90.

Meng, Jinhong et al. "Contribution of human muscle-derived cells to skeletal muscle regeneration in dystrophic host mice." *PloS one* vol. 6,3 e17454. Mar. 9, 2011.

Meyer, Isuzu, and Holly E Richter. "Impact of fecal incontinence and its treatment on quality of life in women." *Women's health (London, England)* vol. 11,2 (2015): 225-38.

Mimura, Toshiki et al. "Diagnostic evaluation of patients with faecal incontinence at a specialist institution." *Digestive surgery* vol. 21,3 (2004): 235-41.

Niessen, Petra et al. "Smoothelin-a is essential for functional intestinal smooth muscle contractility in mice." *Gastroenterology* vol. 129,5 (2005): 1592-601.

Office Action and Search Report issued in Russian Application No. 2020120580/10(035099), dated Jun. 10, 2022. English Translation.

Park, Jung Sik, et al. "Isolation of neural precursor cells from skeletal muscle tissues and their differentiation into neuron-like cells." *Experimental & molecular medicine* 39.4 (2007): 483-490.

Park, Won Sun et al. "Functional expression of smooth muscle-specific ion channels in TOF-β(1)-treated human adipose-derived mesenchymal stem cells." *American journal of physiology. Cell physiology* vol. 305,4 (2013): C377-91.

Popescu, L M et al. "Caveolae in smooth muscles: nanocontacts." *Journal of cellular and molecular medicine* vol. 10,4 (2006): 960-90.

Qu, Zhuqing, et al. "Development of approaches to improve cell survival in myoblast transfer therapy." *The Journal of cell biology* 142.5 (1998): 1257-1267.

Quander, Carline R et al. "Prevalence of and factors associated with fecal incontinence in a large community study of older individuals." *The American journal of gastroenterology* vol. 100,4 (2005): 905-9.

Qu-Petersen, Zhuqing et al. "Identification of a novel population of muscle stem cells in mice: potential for muscle regeneration." *The Journal of cell biology* vol. 157,5 (2002): 851-64.

Ramkumar, D, and K S Schulze. "The pylorus." *Neurogastroenterology and motility : the official journal of the European Gastrointestinal Motility Society* vol. 17 Suppl 1 (2005): 22-30.

Rando and Blau. "Primary mouse myoblast purification, characterization, and transplantation for cell-mediated gene therapy." *Journal of Cell Biology* 125.6 (1994): 1275-1287.

Rao, Satish S C. "Pathophysiology of adult fecal incontinence." *Gastroenterology* vol. 126,1 Suppl 1 (2004): S14-22.

Rochlin, Kate et al. "Myoblast fusion: when it takes more to make one." *Developmental biology* vol. 341,1 (2010): 66-83.

Romaniszyn, Michał, et al. "Implantation of autologous muscle-derived stem cells in treatment of fecal incontinence: results of an experimental pilot study." *Techniques in coloproctology* 19.11 (2015): 685-696.

Sanders, K M. "Regulation of smooth muscle excitation and contraction." *Neurogastroenterology and motility : the official journal of the European Gastrointestinal Motility Society* vol. 20 Suppl 1,Suppl 1 (2008): 39-53.

Sharifiaghdas, Farzaneh et al. "Isolation of human adult stem cells from muscle biopsy for future treatment of urinary incontinence." *Urology journal* vol. 8,1 (2011): 54-9.

Skuk, Daniel et al. "Intramuscular transplantation of myogenic cells in primates: importance of needle size, cell number, and injection volume." *Cell transplantation* vol. 23,1 (2014): 13-25.

Sturgill, Elizabeth R., et al. "Biosynthesis of the major brain gangliosides GD1a and GT1b." *Glycobiology* 22.10 (2012): 1289-1301.

Syverud, Brian C., et al. "Isolation and purification of satellite cells for skeletal muscle tissue engineering." *Journal of regenerative medicine* 3.2 (2014).

Thurner, Marco et al. "Development of an in vitro potency assay for human skeletal muscle derived cells." *PloS one* vol. 13,3 e0194561. Mar. 22, 2018.

(56) References Cited

OTHER PUBLICATIONS

Thurner, Marco et al. "Generation of myogenic progenitor cell-derived smooth muscle cells for sphincter regeneration." *Stem cell research & therapy* vol. 11,1 233. Jun. 12, 2020.
Torrente, Y et al. "Intraarterial injection of muscle-derived CD34(+)Sca-1(+) stem cells restores dystrophin in mdx mice." *The Journal of cell biology* vol. 152,2 (2001): 335-48.
Trébol, Jacobo et al. "Stem cell therapy for faecal incontinence: Current state and future perspectives." *World journal of stem cells* vol. 10,7 (2018): 82-105.
Vaizey, C J et al. "Primary degeneration of the internal anal sphincter as a cause of passive faecal incontinence." *Lancet (London, England)* vol. 349,9052 (1997): 612-5.
Van de Rijn, M et al. "CD34 expression by gastrointestinal tract stromal tumors," *Human pathology* vol. 25,8 (1994): 766-71.
Van Eys, Guillaume J et al. "Smoothelin in vascular smooth muscle cells." *Trends in cardiovascular medicine* vol. 17,1 (2007): 26-30.
Wang, Gang et al. "Origin and differentiation of vascular smooth muscle cells." *The Journal of physiology* vol. 593.14 (2015): 3013-30.
Wang, Jennifer Y, and Maher A Abbas. "Current management of fecal incontinence." *The Permanente journal* vol. 17,3 (2013): 65-73.
Wang, Jiaxu et al. "Multiple roles of alpha-smooth muscle actin in mechanotransduction." *Experimental cell research* vol. 312,3 (2006): 205-14.
Wang, Youwei et al. "Safety of mesenchymal stem cells for clinical application." *Stem cells international* vol. 2012 (2012): 652034.
Wörl, Jürgen et al. "Deletion of Pax7 changes the tunica muscularis of the mouse esophagus from an entirely striated into a mixed phenotype." *Developmental dynamics : an official publication of the American Association of Anatomists* vol. 238,4 (2009): 864-74.
Wright, Woodring E., and Jerry W. Shay. "Historical claims and current interpretations of replicative aging." *Nature biotechnology* 20.7 (2002): 682-688.
Yin, Hang et al. "Satellite cells and the muscle stem cell niche." *Physiological reviews* vol. 93,1 (2013): 23-67.
Krasnopolsky V.I. et al., "Stem cells in the treatment of patients with stress urinary incontinence", Russian Bulletin of an Obstetrician-Gynecologist, 2007, No. 5, 44-47. English Abstract.
Amend, B. et al., "Regeneration of Degenerated Urinary Sphincter Muscles: Improved Stem Cell-Based Therapies and Novel Imaging Technologies," *Cell Transplantation*, 24 (2015): 2171-2183.
Pisani, D. F. et al., "Isolation of a Highly Myogenic CD34-Negative Subset of Human Skeletal Muscle Cells Free of Adipogenic Potential," *Stem Cells*, 28 (2010): 753-764.
Search Report issued in counterpart Chilean Patent Application No. 202102169, issued Sep. 1, 2023.
Huang, et al., *Journal of Hebei Medical University*, 34 (2013): 1231-1234.
Office Action issued in Japanese Application No. 2020-533052, dated Aug. 9, 2022. With English Translation.
Wen, J. et al., "Progress of stress urinary incontinence treatment by using stem cell," *J Mod Urol*, 16 (2011): 93-97.
Birbrair, A. et al., "Skeletal muscle neural progenitor cells exhibit properties of NG2-glia," *Experimental Cell Research*, 319 (2013): 45-63.
Frudinger, A. et al., "Skeletal Muscle-Derived Cell Implantation for the Treatment of Fecal Incontinence: A Randomized, Placebo-Controlled Study," *Clinical Gastroenterology and Hepatology*, 21 (2023): 476-486.
Hirai, H. et al., "Direct reprogramming of fibroblasts into Smooth Muscle-Like Cells with Defined Transcription Factors," *Arterioscler Thromb Vasc Biol.*, 38.9 (2018): 2191-2197.

Incitti, T. et al., "Pluripotent stem cell-derived skeletal muscle fibers preferentially express myosin heavy-chain isoforms associated with slow and oxidative muscles," *Skeletal Muscle*, 10.17 (2020): 1-11.
International Search Report and Written Opinion issued in International Patent Application No. PCT/EP2022/072088, mailed Oct. 17, 2022.
Ito, N. et al., "Direct reprogramming of fibroblasts into skeletal muscle progenitor cells by transcription factors enriched in undifferentiated subpopulation of satellite cells," *Scientific Reports*, 7 (2017): 8097, 1-12.
Jorge, J. et al., "Etiology and Management of Fecal Incontinence," Dis Colon Rectum, 36.1 (1993): 77-96.
Lebedeva, O. C. et al., " Индуцированные плюрипотентные стволовые клетки: новые возможности в нейробиологии и нейротрансплантологии " *Институт молекулярной генетики*, 5.4 (2011): 37-45. No English translation available.
Le Ricousse-Roussanne, S. et al., "Ex vivo generation of mature and functional human smooth muscle cells differentiated from skeletal myoblasts," *Experimental Cell Research*, 313 (2007): 1337-1346.
Li, B-J. et al., "Isolation, Culture and Identification of Porcine Skeletal Muscle Satellite Cells," *Asian Australas. L. Anim. Sci.*, 28.8 (2015): 1171-1177.
Messner, F. et al., „Myogenic progenitor cell transplantation for muscle regeneration following hindlimb ischemia and reperfusion, *Stem Cell Research & Therapy*, 12 (2021): 146, 1-15.
Miyagoe-Suzuki, Y. et al., "Skeletal muscle generated from induced pluripotent stem cells—induction and application," *World Journal of Stem Cells*, 9.6 (2017): 89-97.
Nolazco, G. et al., "Effect of muscle-derived stem cells on the restoration of corpora cavernosa smooth muscle and erectile function in the aged rat," *Journal Compilation, BJU International*, 101 (2008):1156-1164.
Notice of Allowance issued in Russian Patent Application No. 2021129050/10, dated Dec. 8, 2023 (English translation).
Office Action issued in Japanese Patent Application No. 2021-552231, dated Jan. 4, 2023 (with English translation).
Office Action issued in Chinese Patent Application No. 202080021489. 4, dated Jan. 26, 2024 (with English translation).
Opposition against European Patent No. 3724319, dated Jan. 9, 2024.
Rao, S.S.C. et al., "Endpoints for Therapeutic Interventions in Fecal Incontinence: Small Step or Game Changer," *Neurogastroenterol Motil.*, 28.8 (2016): 1123-1133.
Seruya, M. et al., "Clonal Population or Adult Stem Cells: Life Span and Differentiation Potential," *Cell Transplantation*, 13 (2004): 93-101.
Takahashi, K. et al., "Induction of pluripotent stem cells from adult human fibroblasts by defined factors," *Cell*, 131 (2007): 861-872.
Takahashi, K. et al., "Induction of pluripotent stem cells from mouse embryonic and adult fibroblast cultures by defined factors," *Cell*, 126 (2006): 663-676.
Tey, S-R. et al., "Coding Cell Identity of Human Skeletal Muscle Progenitor Cells Using Cell Surface Markers: Current Status and Remaining Challenges for Characterization and Isolation," *Frontiers in Cell and Development Biology*, 7 (2019): Article 284, 1-27.
Wilschut, K. J. et al., "Approaches to isolate porcine skeletal muscle stem and progenitor cells," *Department of Farm Animal Health, Faculty of Veterinary Medicine, Utrecht University*, (2010): 1-13.
Xuan, W. et al., "Pluripotent stem cell-induced skeletal muscle progenitor cells with givinostat promote myoangiogenesis and restore dystrophin in injured Duchenne dystrophic muscle," *Stem Cell Research & Therapy*, 12 (2021): 131, 1-15.
Yamanaka, S., "Induction of pluripotent stem cells from mouse fibroblasts by four transcription factors," *Cell Proliferation*, 41. Suppl 1 (2008): 51-56.

\* cited by examiner

Figure 1
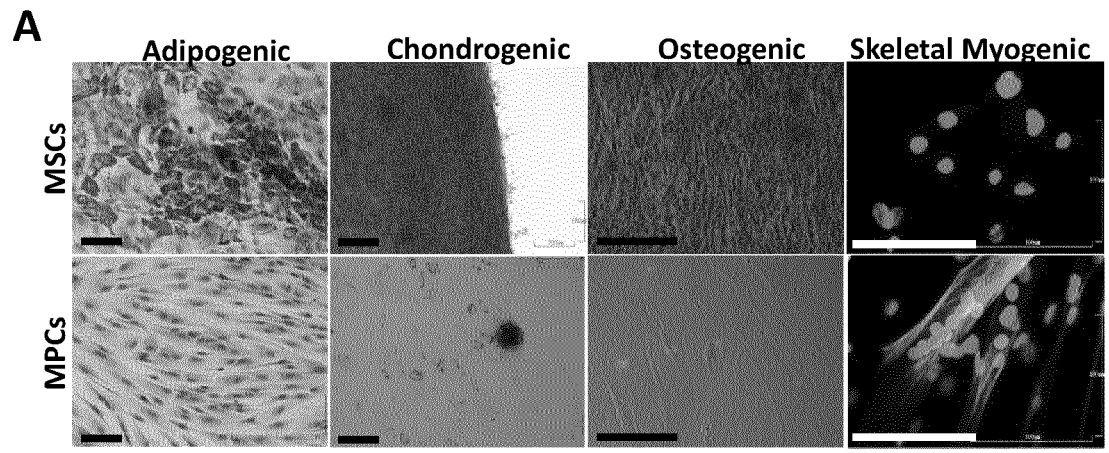
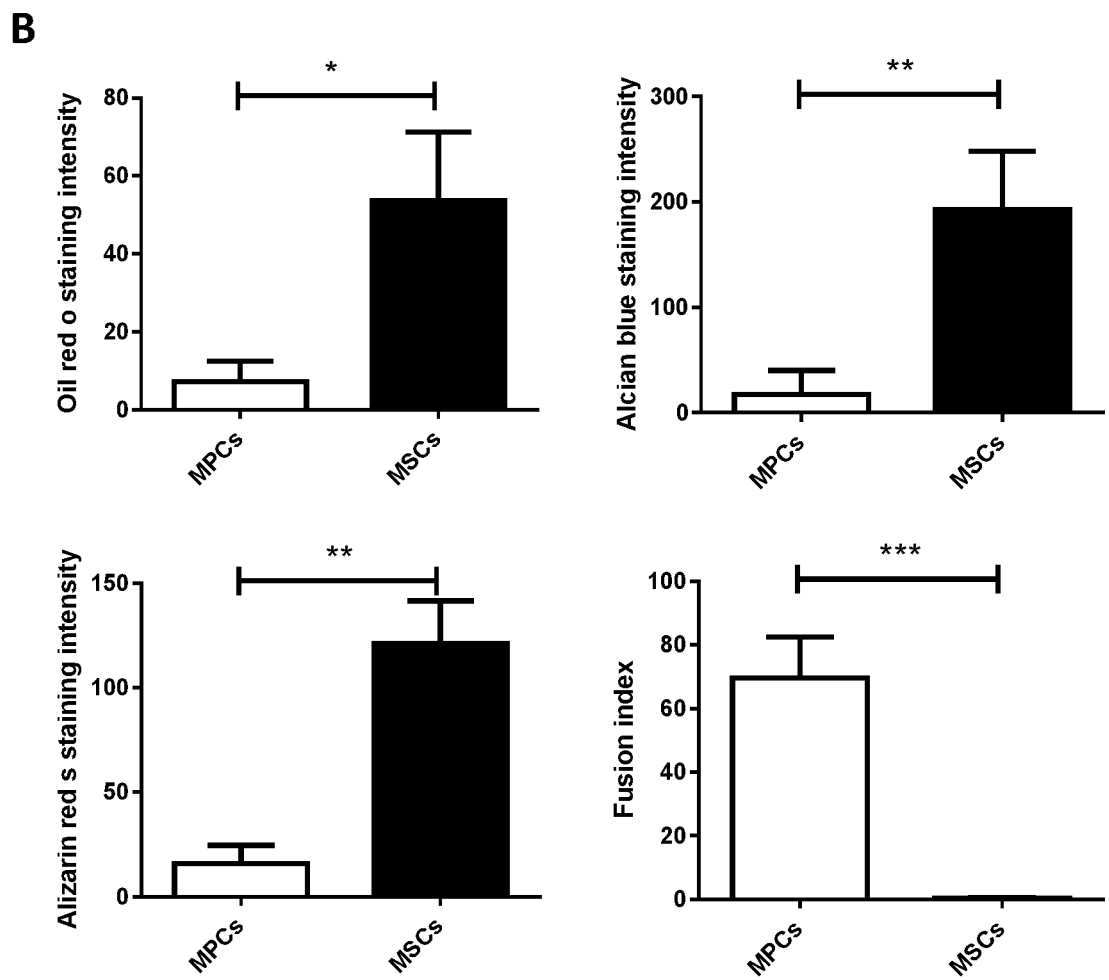

Figure 3
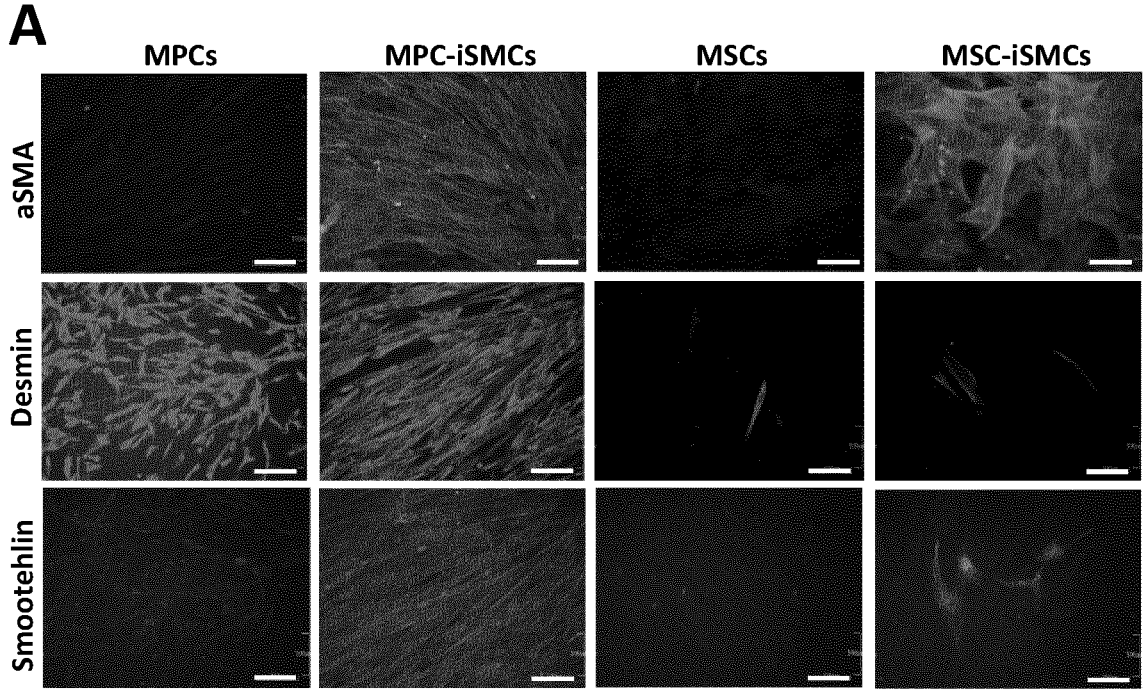
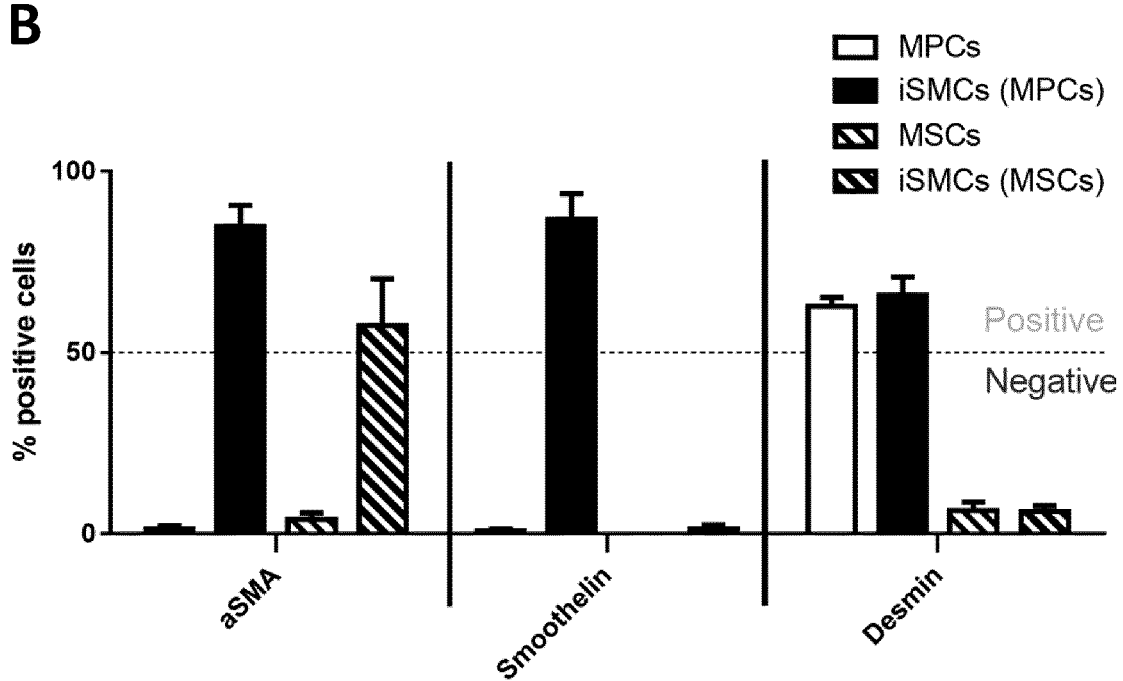

Figure 6
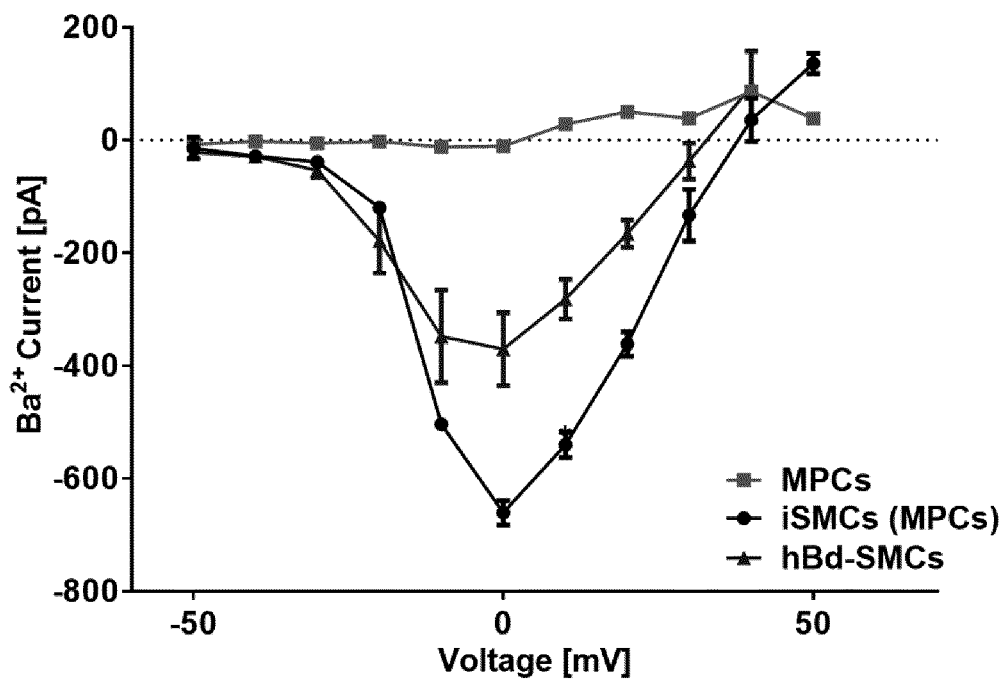
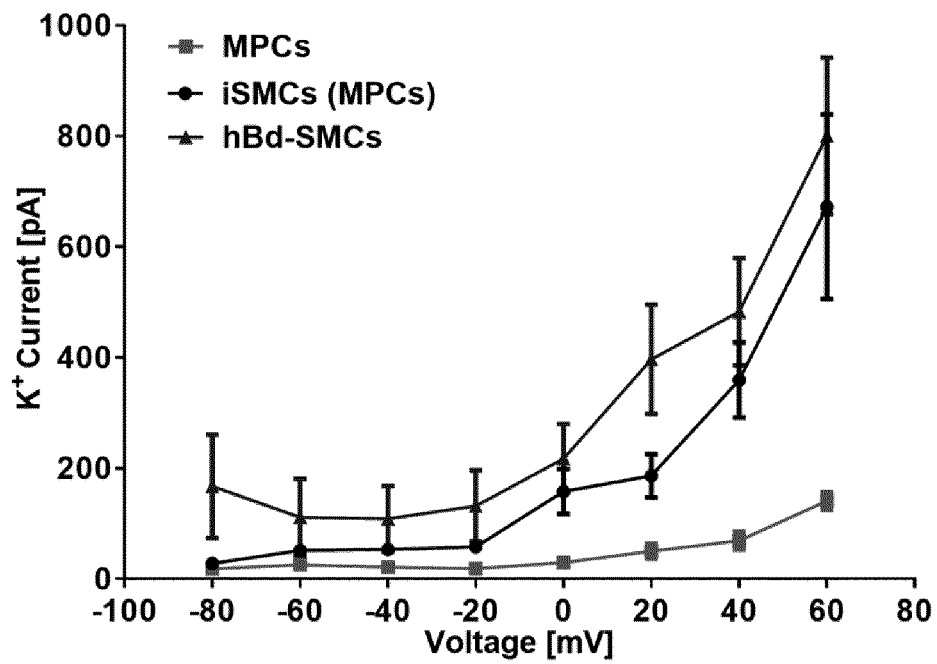

Figure 7
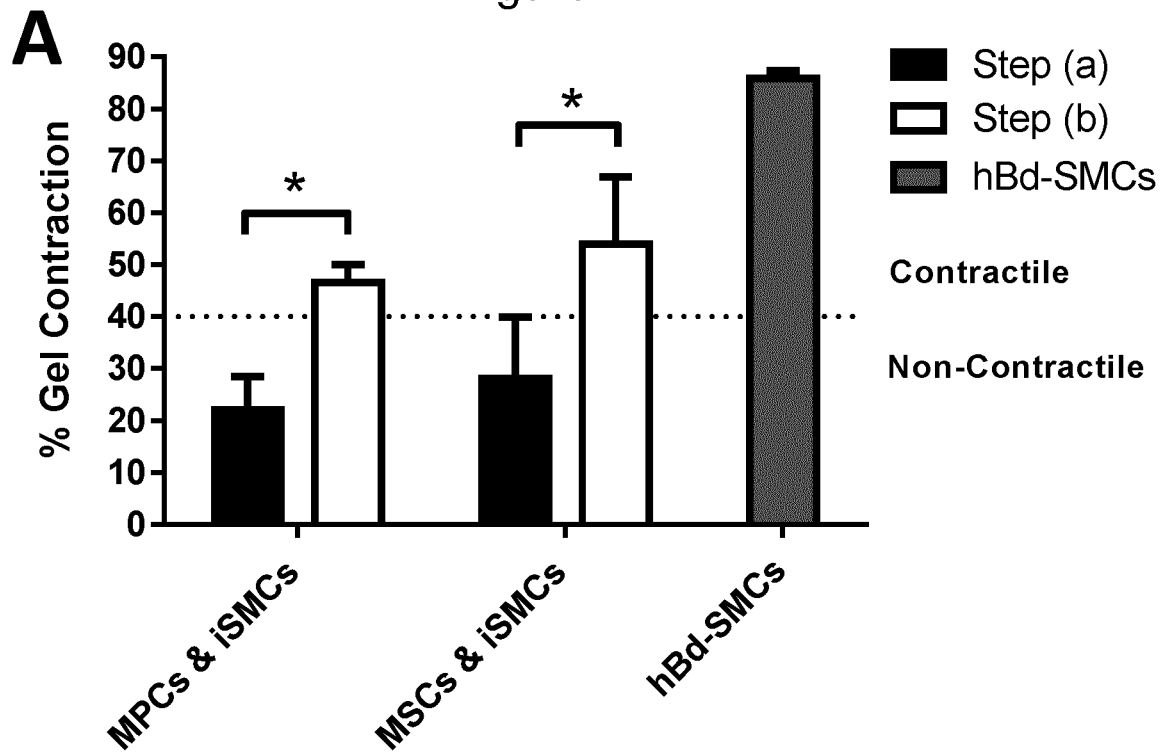
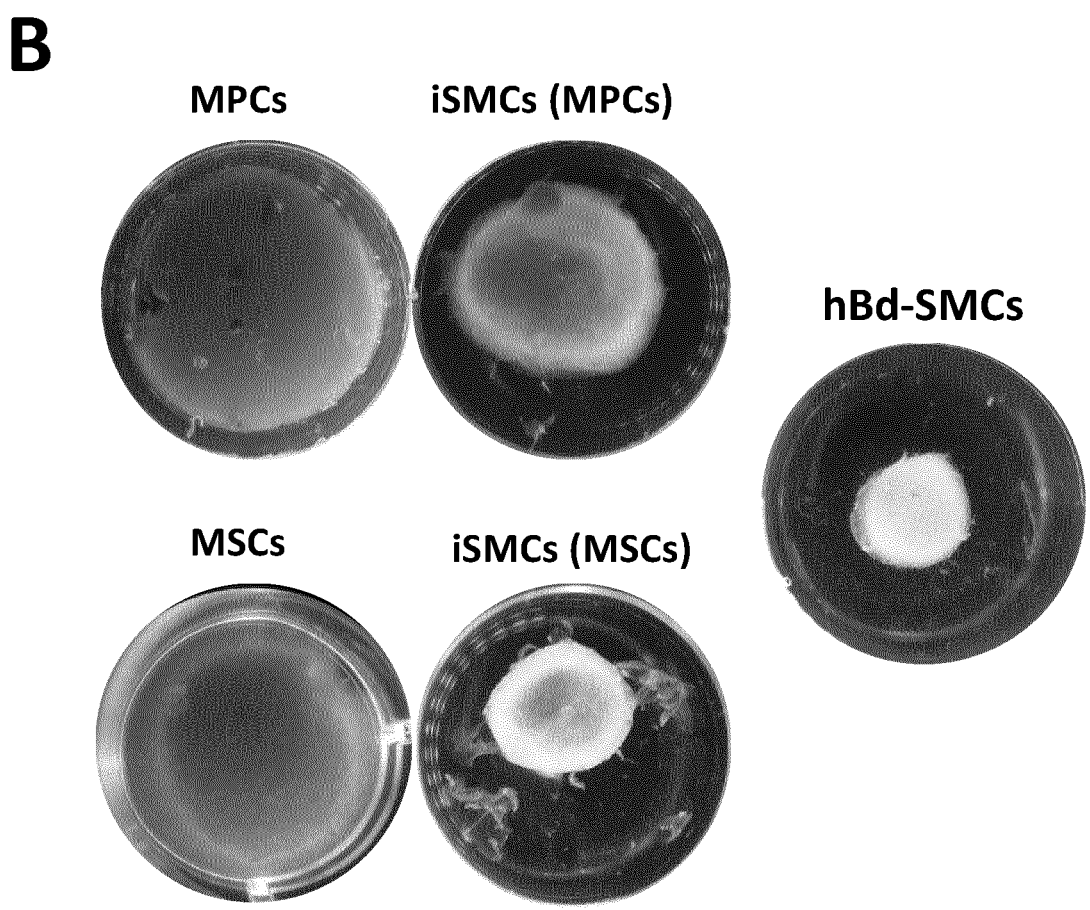

Figure 12

| Gene | MSCs | MPCs | Gene | MSCs | MPCs | Gene | MSCs | MPCs |
|---|---|---|---|---|---|---|---|---|
| ACTA2 | 2.38* | 0.22 | GUCY1B3 | -0.3 | 0.52 | PLA2G6 | -0.04 | -0.15 |
| ACTG2 | 1.89* | 2.86 | ITPR1 | 1.02* | 2.86* | PLCB1 | -1.5 | 1.02* |
| ADCY1 | 0.06 | -0.02 | ITPR2 | 0.98 | 1.06* | PLCB2 | 0.42 | 0.55 |
| ADCY2 | 0 | 1.76* | ITPR3 | -0.25 | -0.04 | PLCB3 | -0.19 | -0.31 |
| ADCY3 | -0.68 | -0.48 | KCNMA1 | 2.93* | 1.91* | PLCB4 | 1.52* | 3.27* |
| ADCY4 | -3.34 | -0.62 | KCNMB1 | 0.03 | 3.85* | PPP1CA | -0.01 | -0.02 |
| ADCY5 | -0.52 | 0.14 | KCNMB2 | -0.51 | 1.24* | PPP1CB | -1.38* | 0.16 |
| ADCY6 | -0.23 | 2.25* | KCNMB3 | -0.26 | 0.08 | PPP1CC | -0.21 | 0.53 |
| ADCY7 | 0.32 | 0.24 | KCNMB4 | 0.48 | 1.74* | PPP1R12A | 0.85 | 1.47* |
| ADCY8 | 0.11 | 0.12 | KCNU1 | 0.49 | 0.08 | PPP1R12B | -0.52 | -1.36 |
| ADCY9 | 0.14 | 0.68 | MAP2K1 | -0.22 | 0.59 | PPP1R12C | -0.1 | 1.16* |
| ADORA2B | -0.66 | -2.81 | MAP2K2 | -0.25 | -0.93 | PPP1R14A | 1.83* | 4.03* |
| ADRA1A | 0.16 | 0.22 | MAPK1 | 1* | 1.44* | PRKACA | -0.13 | 0.29 |
| ADRA1B | 0.14 | -0.41 | MAPK3 | -0.82 | -0.94 | PRKACB | 0.62 | 1.22* |
| ADRA1D | 0.24 | 0.3 | MRVI1 | -0.13 | -0.05 | PRKACG | 0.09 | -0.38 |
| AGTR1 | 0.65 | 0.23 | MYH11 | -0.23 | 0.7 | PRKCA | 0.23 | -0.1 |
| ARAF | 0.04 | 1.65* | MYL6 | 0.11 | 0.37 | PRKCB | -0.1 | 0.44 |
| ARHGEF11 | 0.8 | 1.21* | MYL6B | -0.13 | -1 | PRKCD | 0 | 0.68 |
| ARHGEF12 | 0.38 | 0.01 | MYL9 | 1.5* | 0.49 | PRKCE | 1.02* | -0.32 |
| AVPR1A | 0.1 | 0.2 | MYLK | -0.28 | -0.16 | PRKCG | 0.39 | 0.13 |
| AVPR1B | -0.18 | -0.26 | MYLK2 | 0.59 | 0.38 | PRKCH | -1.14 | -0.1 |
| CACNA1C | -0.06 | 0.23 | MYLK3 | -0.15 | 0.52 | PRKCQ | 0.26 | 0.22 |
| CACNA1D | 0.03 | 0.16 | MYLK4 | -0.1 | 0.28 | PRKG1 | 0.44 | 0.41 |
| CACNA1F | 0.39 | 0.17 | NPR1 | 0.53 | 0.21 | PTGIR | -0.37 | 0.41 |
| CACNA1S | 0.4 | -0.41 | NPR2 | 0.02 | 0.31 | RAF1 | -0.43 | -0.73 |
| CALCRL | 0.69 | 2.22 | PLA2G10 | -0.14 | -0.34 | RAMP1 | -0.36 | -0.34 |
| CALD1 | 1.21* | 1.36* | PLA2G12A | 0.09 | 0.79 | RAMP2 | -0.1 | -0.31 |
| CALM2 | 0.42 | 0.42 | PLA2G12B | -0.14 | -0.02 | RAMP3 | 0.06 | 0.43 |
| CALML3 | -0.07 | 0.2 | PLA2G1B | -0.09 | 0.45 | RHOA | 0.63 | 0.56 |
| CALML4 | -0.66 | 0.4 | PLA2G2A | -4.99 | -1.18 | ROCK1 | -0.21 | 0.22 |
| CALML5 | -0.2 | -0.12 | PLA2G2C | 0.11 | -0.21 | ROCK2 | 0.03 | 0.84 |
| CALML6 | 0.56 | -0.14 | PLA2G2D | 0.08 | 0.39 | ROCK2 | 0.42 | 0.84 |
| CYP4A11 | 0.16 | 0.38 | PLA2G2E | 0.01 | 0.02 | CNN1 | 4.06* | 1.8* |
| EDNRA | 0.19 | -0.1 | PLA2G2F | 0.51 | -0.17 | DES | -0.36 | 0.08 |
| GNA11 | 0.48 | 0.01 | PLA2G3 | -0.02 | 0.26 | TPM1 | 1.96* | 0.61 |
| GNA12 | 0.56 | 0.32 | PLA2G4A | -1.46 | 0.26 | SMTN | -0.29 | 1.02* |
| GNA13 | 0.83 | 1.88* | PLA2G4C | -0.25 | -0.1 | TAGLN | 1.06* | 0.14 |
| GNAQ | 1.44* | 0.88 | PLA2G4D | -0.03 | 0.33 | VCL | -0.3 | -0.16 |
| GNAS | 0.2 | 0.51 | PLA2G4E | -0.37 | 0.07 | ITGA3 | 0.74 | 0.84 |
| GUCY1A2 | -0.11 | -0.3 | PLA2G4F | -0.29 | 0.2 | ITGA1 | 2.77* | 1.51* |
| GUCY1A3 | 0.05 | 1.7* | PLA2G5 | -1.18 | 0.16 | MCAM | 0.17 | 0.6 |

Figure 13
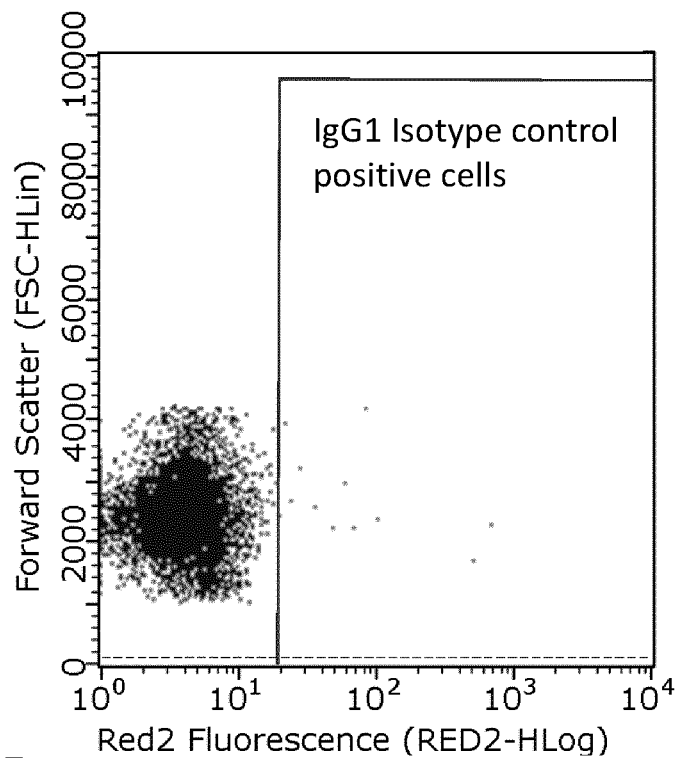
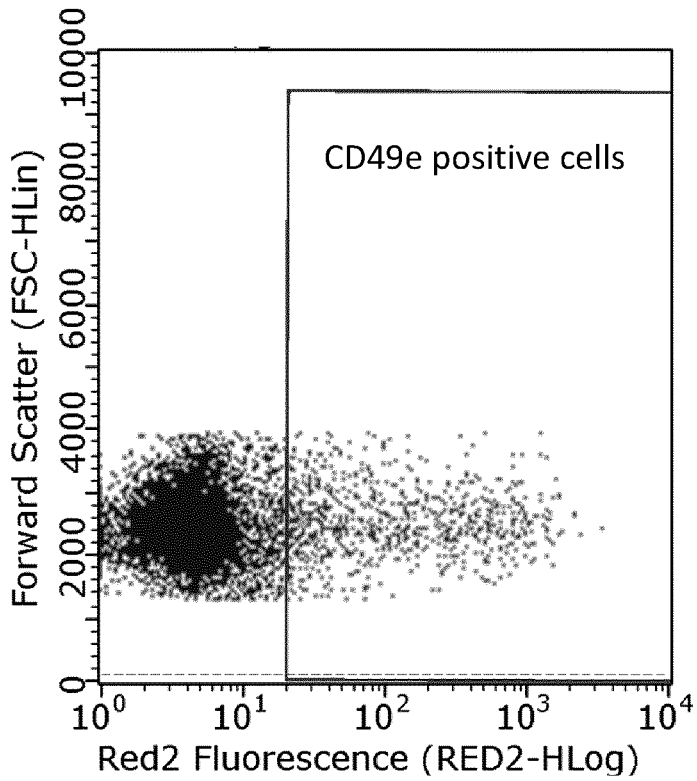

| Marker | CD56+ SMDC (Thurner et al 2018) | CD56- SMDC (Thurner et al. 2018) | SMDC (Frudinger et al. 2018) | MPCs | MSCs | MPC-iSMCs | MSC-iSMCs |
|---|---|---|---|---|---|---|---|
| Skeletal myogenic | yes | no | yes | yes | no | no | no |
| Multipotent | no | yes | no | no | yes | no | no |
| CD105 | + | + | + | + | + | + | + |
| CD90 | + | + | + | + | + | + | + |
| CD73 | + | + | + | + | + | + | + |
| CD56 | + | , | + | , | , | + | , |
| CD34 | , | , | , | , | , | , | , |
| CD146 | , | , | , | + | , | + | + |
| CD49a | , | , | , | + | , | + | + |
| aSMA | , | , | , | + | , | + | + |
| Desmin | + | , | + | + | , | + | , |
| ACHE | + | , | + | + | , | , | , |
| CK | + | , | + | + | , | , | , |

Figure 15

METHODS FOR OBTAINING INDUCED SMOOTH MUSCLE CELLS

This application is a national phase application under 35 U.S.C. § 371 of International Application No. PCT/EP2020/057940, filed Mar. 23, 2020, which claims benefit of priority to European Application No. 19164574.6, filed Mar. 22, 2019. The entire contents of each of the aforementioned applications is hereby incorporated by reference.

The present invention relates to methods for obtaining induced smooth muscle cells (iSMCs), iSMCs, iSMCs for use in a method of treating a disease or disorder or for use in tissue engineering, and the use of skeletal muscle derived cells for obtaining iSMCs.

Degeneration of smooth muscles e.g. in sphincters can cause debilitating diseases such as fecal incontinence. Skeletal muscle derived cells (SMDCs) have been effectively used in the clinics for regeneration of the skeletal muscle sphincters, such as the external anal or urinary sphincter. However, little is known about the in vitro smooth muscle differentiation and in vivo smooth muscle regenerative potential of SMDCs derived smooth muscle cells.

Sphincters are circular muscles controlling the movement of solids and/or liquids and can consist of either skeletal muscle, such as the external anal sphincter or smooth muscle, such as the internal anal and pyloric sphincter (Al-Ali et al., 2009; Ramkumar & Schulze, 2005). Malfunction of the sphincter muscles of the anus and the pylorus is associated with fecal incontinence and gastroparesis, respectively (Abrahamsson, 2007; Rao, 2004). Degeneration of smooth muscle of the internal anal sphincter is a known cause of passive fecal incontinence (Vaizey et al., 1997), the main type of fecal incontinence, affecting 78% of all fecal incontinence patients (Mimura et al., 2004). Although not life threatening, fecal incontinence severely affects patients' quality of life (Meyer & Richter, 2015) and has a prevalence rate of up to 12% in men and women (Goode et al., 2005; Quander et al., 2005). Conservative treatments such as application of bulking agents have limited success in patient with high incontinence severity and surgical approaches have high morbidity and complication rates (J. Y. Wang & Abbas, 2013).

Functionality of smooth muscle tissue relies on the existence of highly differentiated smooth muscle cells expressing contractile proteins such as smooth muscle actin alpha (aSMA), desmin and smoothelin (SMTN) (Capetanaki et al., 1997; van Eys et al., 2007; J. Wang et al., 2006) as well as functional voltage gated calcium and potassium channels, enabling the induction of regulated cell contraction (Sanders, 2008). The isolation and use of similar cells for treatment of smooth muscle deficiencies might be a promising treatment option. However, no smooth muscle cell therapy is currently available on the market. The isolation of smooth muscle cells able to regenerate deficient smooth muscle tissue is a first prerequisite for approaching clinical use of these cells. A state of the art method to derive smooth muscle cells is the use of smooth muscle tissue as a source. These primary smooth muscle cells were effectively used for smooth muscle regeneration in a passive fecal incontinence animal model (Bohl et al., 2017), however primary smooth muscle cells are hardly accessible in living humans for autologous treatment, heterogeneous in nature and may be limited in proliferative capacity (Sandison & McCarron, 2015), thus qualify less as cell therapeutic candidate for smooth muscle regeneration in human. Thus, the use of highly proliferative stem/progenitor cells ready to differentiate to smooth muscle cells was approached.

Stem/progenitor cells such as multipotent mesenchymal stromal cells (MSCs) and induced pluripotent stem cells (iPSCs) have been shown to harbor transdifferentiation potential towards the smooth muscle lineage (Bajpai et al., 2012; Park et al., 2013) as well as in vivo smooth muscle regenerative potential (Li et al., 2016). iPSCs especially are promising in their smooth muscle differentiation potential and functionality in vitro (Bajpai et al., 2012) and iPSCs derived smooth muscle progenitor cells demonstrated urethral sphincter regenerative potential in vivo (Li et al., 2016), however, concerns on safety, such as genetic instability and teratoma formation, limit their usefulness (Jung et al., 2012). Adult MSCs derived cell products did not cause major health concerns in the majority of clinical trials (Y. Wang et al., 2012). However, their clinical efficacy in smooth muscle regeneration remains elusive.

Skeletal muscle tissue was found to be a source of stem and progenitor cells such as MSCs and satellite cell-derived myogenic progenitors, both expected to be highly regenerative (Yin et al., 2013). Skeletal muscle-derived cells (SMDCs) enriched for CD56positive cells have been shown to improve external anal sphincter weakness associated fecal incontinence in the clinics (A. Frudinger et al., 2010, 2015; Andrea Frudinger et al., 2018). Furthermore, skeletal muscle-derived cells were found to engraft into the bladder detrusor muscle improving bladder function (Huard et al., 2002). However, limited knowledge exists regarding the SMDCs to smooth muscle cell differentiation and isolation thereof or their regenerative capacity in vivo (Lu et al., 2011) and no study has evaluated the therapeutic potential of SMDCs derived smooth muscle cells (induced smooth muscle cells) for sphincter smooth muscle regeneration.

Cell therapeutic approaches for regeneration of smooth muscle tissue are highly desirable and rely on the use of cells competent for smooth muscle regeneration. In view of the drawbacks of the prior art methods, new methods for the provision of smooth muscle cells are needed.

Frudinger et al. (2018) teaches the isolation of CD56+ skeletal muscle derived cells called SMDCs as shown in FIG. 6 of Frudinger et al. (2018) (Andrea Frudinger et al., 2018). Said cells are characterized amongst others by a negative expression of aSMA, CD49a, and CD146 as shown in FIG. 17 of the present disclosure. In addition, as stated in Frudinger et al. (2018) the SMDCs are characterized by a positive expression of Pax-7 (Andrea Frudinger et al., 2018). The SMDCs described in Frudinger et al. (2018) are skeletal-myogenic, i.e. they are able to fuse to multinucleated myotubes.

EP 2 206 774 A1 relates to cell populations having differentiation capacities which are obtainable by isolation from a muscle tissue, more particularly from a skeletal and/or cardiac muscle tissue, preferably from endomysial and/or cardiac tissue (Marolleau et al., 2010). The cell population of EP 2 206 774 A1 comprises ALDH-positive cells and notably have myogenic and/or adipogenic and/or osteogenic differentiation capacities. In particular, EP 2 206 774 A1 discloses ALDH+/CD34− cells, ALDH+/CD34+ cells and SMALD/34+ cells which all are CD146− as shown in Tables 1 and 3 and FIG. 8 of EP 2 206 774 A1. In addition, EP 2 206 774 A1 discloses SMALD/34− cells. Said cells are CD146+ and fusion competent as shown in FIG. 3 of EP 2 206 774 A1.

Lecourt S et al. (2010) investigates that human skeletal muscle is an essential source of various cellular progenitors with potential therapeutic perspectives. On the one hand CD56+ cells are described which are CD49a− and CD49e+

.On the other hand CD56− cells are described which are CD146− and SMA− (Lecourt et al., 2010).

Thurner et al. (2018) discloses the development of an in vitro potency assay for human skeletal muscle derived cells. In particular, the isolation of both CD56+ and CD56− skeletal muscle derived cells (SMDCs) are described. As shown in FIG. 17 of the present disclosure both CD56+ and CD56− SMDCs described in Thurner et al. (2018) are aSMA−, CD146− and CD49a−. In addition, as shown in FIG. 2a in Thurner et al. (2018), the CD56+ cells have an AChE activity of >1000 mUrel/g.

The present invention underlies the technical problem to provide a method to obtain iSMCs that are safe and effective for use in a method of treating a disease or disorder in a subject. A further technical problem underlying the present invention is the provision of cells which are safe and effective for use in regenerating smooth muscle tissue.

This technical problem is solved by the subject-matter defined in the claims.

The following figures form part of the present specification and are included to further demonstrate certain aspects of the present invention. The invention may be better understood by reference to one or more of these drawings in combination with the detailed description of specific embodiments presented herein.

FIG. 1 illustrates the characterization of skeletal muscle derived MPCs and MSCs according to their differentiation potential. Differentiation potential of MPCs and MSCs, assessed after in vitro differentiation to adipogenic, chondrogenic, osteogenic and skeletal myogenic lineages by cultivation in respective differentiation media and detected by oil red o (adipocytes), alcian blue (chondrocytes), alizarin red s (osteocytes) and anti-desmin/Hoechst (nuclei and myocytes) staining, respectively. Representative images (scale bar=100 µm) of at least three individual preparations are shown (A). Quantification of adipogenic-, chondrogenic-, osteogenic- and skeletal myogenic differentiation potential of MSCs and MPCs by calculation of mean staining intensity per field of oil red o, alcian blue or alizarin red s staining or by fusion index calculation of at least three individual samples, respectively (B). Data are presented as mean±SD of MPCs and MSCs from at least three individual muscle biopsies. Statistical comparison was performed by unpaired t-tests (p<0.05 considered significant).

FIG. 2 illustrates the characterization of skeletal muscle derived MPCs and MSCs and the iSMCs derived thereof by their cell surface marker expression. Surface expression of mesenchymal (CD105, 90, 73), myogenic (CD56), hematopoietic (CD34) and smooth muscle lineage markers (CD146 and CD49a) on skeletal muscle derived MPCs and MSCs as well as iSMCs derived thereof from each at least three individual human skeletal muscle biopsies assessed by flow cytometry. As a control, expression of smooth muscle lineage markerCD146 and CD49a is demonstrated in populations of human bladder derived smooth muscle cells (hBd-SMCs). Data are presented as mean±SEM.

FIG. 3 illustrates the expression of intracellular markers in SMDCs (MPCs and MSCs) and iSMCs. Detection of general myogenic (Desmin) and smooth muscle myogenic (aSMA, Smoothelin) markers in MPCs and MSCs as well as iSMCs derived thereof was performed by immunocytochemistry and representative images (scale bar=100 µm) are shown (A). Percent of cells positive for aSMA, Smoothelin or Desmin within MPCs, MSCs and iSMCs derived thereof as assessed by quantification of corresponding marker expressing cells on immunocytochemistry images of cultures from at least three individual human muscle biopsies (B). Data are presented as mean±SEM.

FIG. 4 illustrates the changes in gene expression during transdifferentiation of SMDCs (MPCs and MSCs) to iSMCs. Changes in gene expression were assessed by microarray analysis of MSCs and MPCs to MSC-iSMCs and MPCs-iSMCs, cultivated in growth (MSCs and MPCs) or smooth muscle differentiation medium (MSCs-iSMCs and MPCs-iSMCs) for 6 days, respectively, derived from two individual human muscle biopsies. Cluster of genes similarly upregulated (A) or downregulated (B) in both MSCs and MPCs upon iSMCs differentiation obtained by k-means clustering are depicted in heat-maps. Asterisks (*) mark genes, which were either up- (log 2 FC≥1) or downregulated (log 2 FC≤−1) in both cell types. Statistical comparison was performed by chi-squared test considering a p-value below 0.05 as significant. Results of the change in gene expression are shown in (C).

FIG. 5 illustrates the fusion competency of MPCs and iSMCs. Formation of myotubes (Fusion competency) was observed by fluorescence microscopy following Hoechst33342 staining for visualization of nuclei. Based on the images, fusion index (FI) (A) and number of nuclei per tube was determined (B). Cells with at least 3 nuclei were counted as tubes. Measurements were compared between MPCs and iSMCs derived thereof.

FIG. 6 illustrates the formation of functional ion channels during MPCs to iSMC transdifferentiation. Analysis of voltage dependent inward calcium (A) and outward potassium currents (B) in MPCs and iSMCs derived thereof as well as bladder derived smooth muscle cells (hBd-SMCs). Impedance-voltage (I-V) curves of each at least three cells of MPCs, iSMCs (derived from MPCs) and hBd-SMCs demonstrate presence of functional $Ca_v$ (A) and $K_v$ (B) channels in iSMCs (derived from MPCs) and hBd-SMCs but not MPCs.

FIG. 7 illustrates the contractility of SMDCs and iSMCs in collagen gel lattices. Contractility of SMDCs (MSCs and MPCs), iSMCs derived thereof and bladder derived smooth muscle cells (hBd-SMCs) quantified by collagen gel lattice contraction. Percent gel contraction from original size within 48 hours of cells obtained by step (a) of the present invention (MPCs or MSCs) and cells obtained by transdifferentiation to iSMCs by step (b) of the present invention as well as control smooth muscle cells from human bladder (hBd-SMCs) shown as bar graph (A). Data presented as Mean±SEM of cell preparations from each at least three individual human muscle biopsies or hBd-SMC analysis. Representative stereomicroscopic images of the collagen gels with embedded MSCs and MSCs and iSMCs each derived thereof as well as hBd-SMCs in wells of a 24-well plate (B).

FIG. 8 illustrates the smooth muscle cell phenotype of mMPCs derived iSMCs and their engraftment into smooth muscle tissue in vivo. Percentage of Desmin and aSMA positive cells in iSMCs derived from murine MPCs depicted as bar graph (A). Fluorescence signal detection of fluorescent beads and TdTomato transgene expressing localization in intact pyloric sphincter muscle by in vivo imaging (B). Alpha smooth muscle actin (aSMA) protein expression, TdTomato expression, of engrafted iSMCs, and overlay (MERGE) of TdTomato and aSMA protein was detected by immunohistochemistry in pyloric sphincter histological sections 12 weeks after implantation. Counterstaining of nuclei in each image was performed by DAPI. Representative images of n=8 injected mice are shown (C).

FIG. 9 illustrates light and scanning electron microscopic images of tissue rings. Light microscopic images of a tissue ring obtained by 3D cultivation of MPCs derived iSMCs located around the central post of an agarose template at different magnifications (A and B). Scanning electron microscopic images of a tissue ring obtained by 3D cultivation of MPCs derived iSMCs at different magnifications (C and D).

Images obtained by transmission electron microscopy of ultrathin sectioned tissue rings obtained by 3D cultivation of iSMCs showing calveolae (arrowheads) on the cell membrane of two adjacent cells (A and B), abundant filamentous structures within the cytoplasm (C) and to dense bodies accumulated filaments (arrows) (D).

FIG. 12 lists the quantification of changes in gene expression during transdifferentiation of SMDCs (MPCs and MSCs) to iSMCs. Changes in gene expression were assessed by microarray analysis of MSCs and MPCs to MSC-iSMCs and MPCs-iSMCs, cultivated in growth (MSCs and MPCs) or smooth muscle differentiation medium (MSCs-iSMCs and MPCs-iSMCs) for 6 days, respectively, derived from two individual human muscle biopsies. Log 2 fold changes of smooth muscle associated genes in MSCs vs MSC-iSMCs (MSCs) and MPCs vs MPCs-iSMCs (MPCs) samples to compare smooth muscle differentiation between MSCs and MPCs are shown. Asterisks (*) mark genes that are up- (Log 2≥1) or down- (Log 2≤−1) regulated.

FIG. 13 illustrates the flow cytometric analysis of anti-CD49e antibody stained and isotype control stained murine MPC-iSMCs according to example 15.

Dot-plots of IgG1 isotype control (A) and anti-CD49e (B) positive MPC-iSMCs demonstrating 0.14% control and 9.5% CD49e positive cells, respectively.

Figure 14:
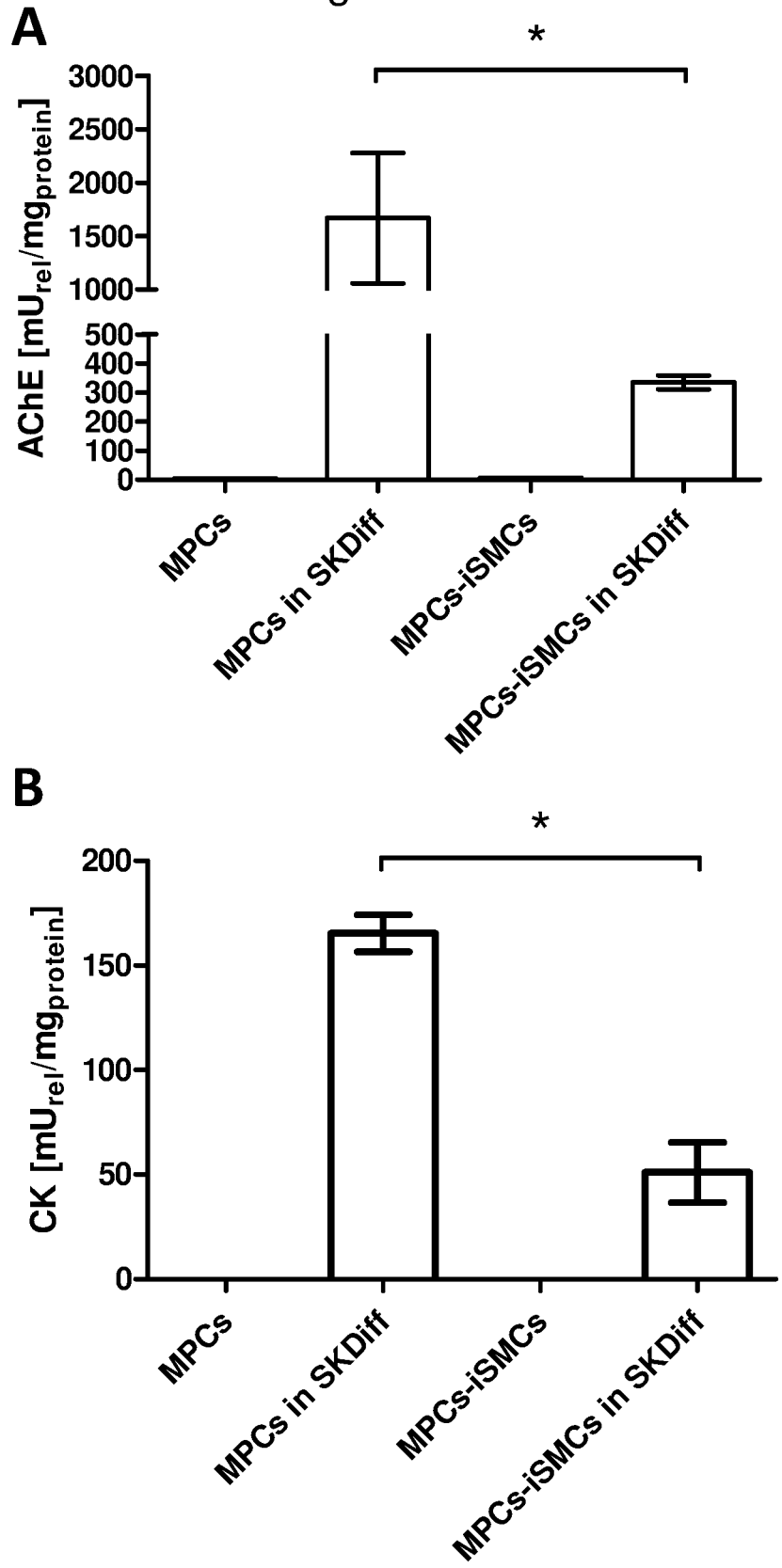

FIG. 14 illustrates the AChE and CK activity analysis of MPCs and MPC-iSMCs, whereby enzyme activities were measured before and after cultivation of cells in skeletal muscle differentiation medium (SKDiff)

AChE activity (A) and CK activity (B) was measured and compared in MPCs and MPC-iSMCs each before and after cultivation in skeletal muscle differentiation medium (SKDiff) for 6 days. Data presented as mean±SEM of cells derived from at least three individual human muscle biopsies. Statistical analysis performed by paired t-test considering p<0.05 as significant.

FIG. 15 provides an overview of properties and marker expression of the distinct cell types described herein. The CD56+ SMDC and CD56− SMDC (Thurner et al 2018) and the SMDC (Frudinger et al. 2018) were obtained as described in Example 18. The MPCs and MSCs were obtained as described in Example 1. The MPC-iSMCs and MSC-iSMCs were obtained as described in Example 2. The expression of a certain marker is indicated as "+", if at least 50% of the cells of the tested cell population expressed the respective cell marker. The expression of a certain marker is indicated as "−", if less than 50% of the cells of the tested cell population expressed the respective cell marker. The AChE enzyme activity of a certain cell population is indicated as "+" if the cell population has an AChE activity of at least 1000 mUrel/mg protein, measured according to Example 17. The AChE enzyme activity of a certain cell population is indicated as "−", if the cell population has an AChE activity of less than 1000 mUrel/mg protein measured according to Example 17. The CK enzyme activity of a certain cell population is indicated as "+" if the cell population has a CK activity of at least 100 mUrel/mg protein, measured according to Example 17. The CK enzyme activity of a certain cell population is indicated as "−", if the cell population has a CK activity of less than 100 mUrel/mg protein measured according to Example 17.

The use of the word "a" or "an" when used in conjunction with the term "comprising" in the claims and/or the specification may mean "one," but it is also consistent with the meaning of "one or more," "at least one," and "one or more than one".

The term "about" means that the value stated, plus or minus 5% of the stated value, or the standard error for measurements of the given value, are contemplated.

The term "anal incontinence," as used herein, refers to any undesired loss of intestine content through the anus, like flatus, liquid or solid faeces. The term comprises all three severity grades: Grade 1=only gaseous, grade 2=liquid and soft feces, grade 3=solid, formed feces.

The term "anal sphincter" or "anal sphincter apparatus," as used herein, refers in particular to the *Musculus sphincter ani externus* and the *Musculus puborectalis* as a part of the *Musculus levator ani*. However it also includes *M. pubococcygeus, M. ischiococcygeus, M. iliococcygeus* and *N. pudendus*.

The term "skeletal muscle derived cells" or "SMDCs" refers to cells obtained from skeletal muscle tissue comprising fusion competent cells as e.g. myoblasts or non-fusion competent cells as e.g. multipotent mesenchymal stromal cells, which can be primary cells and/or in vitro cultured cells and alternatively to other cells with myogenic or multi differentiation potential (e.g., from liposuctioned tissue or other stem cell harbouring tissues such as bone marrow). The term also comprises cells derived from adipose which can be isolated and used for differentiation to smooth muscle cells. The term "skeletal muscle derived cells" or "SMDCs" also refers to a cell population isolated from muscle tissue.

The term "human bladder derived smooth muscle cells (hBd-SMCs)" refers to populations of cells comprising smooth muscle cells from the human bladder. hBd-SMCs are commercially available from PromoCell® (Catalogue number: C-12571) and represent the phenotypic and functional characteristics of smooth muscle cells that in the present invention are foreseen to be obtained by iSMCs derived from skeletal muscle derived cells.

The term "injection" as used herein, refers to the expulsion of an injection solution comprising above mentioned cells out of an injection device into a specific site within the human body, in particular into or adjacent to muscle-tissue providing for anal continence. The injection process can be, but is not limited to, static, i.e., the injection device remains at the position reached. Alternatively, the injection process is dynamic. For instance, in some embodiments of the present invention the injection occurs simultaneously with the retraction of the injection device from the site of injection.

The term "injection site" as used herein, refers to a site within the human body, such as close to or being muscle-tissue providing for anal continence, at which the injection process is initiated. The injection site needs not to be identical with the site where the injection process ends.

The term "injection device" as used herein, refers to any device suitable for penetrating human tissue in order to reach an injection site of interest and capable of delivering solutions, in particular solutions comprising muscle-derived cells to the injection site of interest.

The term "faeces incontinence" as used herein, refers only to the undesired loss of liquid or formed faeces through the anus.

The term "passive incontinence" as used herein, refers to a lack of sensory recognition of loss of faeces. This comprises low anal base line pressure values, due to defective internal anal sphincter smooth muscle, and/or a lacking sensoric ability of the anal and rectal mucosa.

The term "CD56+" or "CD56 positive" as used herein refers to a cell expressing the cell marker CD56. The terms "CD56+" or "CD56 positive" can also be used for a cell population comprising different cell types, if preferably at least 50, 60, 70, 80, 90, 95, 98 or 99 percent of the cell population express the cell marker CD56.

The term "CD56–" or "CD56 negative" as used herein refers to a cell not expressing the cell marker CD56. The terms "CD56–" or "CD56 negative" can also be used for a cell population comprising different cell types, if preferably less than 50% or at most 49, 40, 30, 20, 10, 5, 4, 3, 2, 1 or 0 percent of the cell population express the cell marker CD56.

The term "multipotent" as used herein refers to the differentiation potential of mesenchymal cells characterized by in vitro differentiation potential at least towards adipogenic-, chondrogenic- and osteogenic-lineages.

The term "oligopotent" as used herein refers to the differentiation potential of mesenchymal cells characterized by in vitro differentiation potential limited to the myogenic lineages such as smooth, striated and cardiac muscle.

The term "mesenchymal cells" as used herein refers to cells positive for CD105, CD90, and CD73 and negative for CD14, CD19, CD34, CD45 and HLA-DR (MHCII).

The term "CD34+" or "CD34 positive" as used herein refers to a cell expressing the cell marker CD34. The terms "CD34+" or "CD34 positive" can also be used for a cell population comprising different cell types, if preferably at least 80, 90, 95, 98 or 99 percent of the cell population express the cell marker CD56.

The term "CD34–" or "CD34 negative" as used herein refers to a cell not expressing the cell marker CD34. The terms "CD34–" or "CD34 negative" can also be used for a cell population comprising different cell types, if preferably less than 50% or at most 49, 40, 30, 20, 10, 5, 4, 3, 2, 1 or 0 percent of the cell population express the cell marker CD34. In a particularly preferred embodiment, the term "CD34–" or "CD34 negative" can be also used for a cell population comprising different cells, if preferably at most 19, 10, 5, 4, 3, 2, 1 or 0 percent of the cell population express the cell marker CD34.

The term "CD146+" or "CD146 positive" as used herein refers to a cell expressing the cell marker CD146. The terms "CD146+" or "CD146 positive" can also be used for a cell population comprising different cell types, if preferably at least 50, 60, 70, 80, 90, 95, 98 or 99 percent of the cell population express the cell marker CD146.

The term "CD146–" or "CD146 negative" as used herein refers to a cell not expressing the cell marker CD146. The terms "CD146–" or "CD146 negative" can also be used for a cell population comprising different cell types, if preferably less than 50% or at most 49, 40, 30, 20, 10, 5, 4, 3, 2, 1 or 0 percent of the cell population express the cell marker CD146.

The term "CD49a+" or "CD49a positive" as used herein refers to a cell expressing the cell marker CD49a. The terms "CD49a+" or "CD49a positive" can also be used for a cell population comprising different cell types, if preferably at least 50, 60, 70, 80, 90, 95, 98 or 99 percent of the cell population express the cell marker CD146.

The term "CD49a–" or "CD49a negative" as used herein refers to a cell not expressing the cell marker CD49a. The terms "CD49a–" or "CD49a negative" can also be used for a cell population comprising different cell types, if preferably less than 50% or at most 49, 40, 30, 20, 10, 5, 4, 3, 2, 1 or 0 percent of the cell population express the cell marker CD49a.

The term "CD73+" or "CD73 positive" as used herein refers to a cell expressing the cell marker CD73. The terms "CD73+" or "CD73 positive" can also be used for a cell population comprising different cell types, if preferably at least 50, 60, 70, 80, 90, 95, 98 or 99 percent of the cell population express the cell marker CD73.

The term "CD73–" or "CD73 negative" as used herein refers to a cell not expressing the cell marker CD73. The terms "CD73–" or "CD73 negative" can also be used for a cell population comprising different cell types, if preferably less than 50% or at most 49, 40, 30, 20, 10, 5, 4, 3, 2, 1 or 0 percent of the cell population express the cell marker CD73.

The term "CD90+" or "CD90 positive" as used herein refers to a cell expressing the cell marker CD90. The terms "CD90+" or "CD90 positive" can also be used for a cell population comprising different cell types, if preferably at least 50, 60, 70, 80, 90, 95, 98 or 99 percent of the cell population express the cell marker CD90.

The term "CD90–" or "CD90 negative" as used herein refers to a cell not expressing the cell marker CD90. The terms "CD90–" or "CD90 negative" can also be used for a cell population comprising different cell types, if preferably less than 50% or at most 49, 40, 30, 20, 10, 5, 4, 3, 2, 1 or 0 percent of the cell population express the cell marker CD105.

The term "CD105+" or "CD105 positive" as used herein refers to a cell expressing the cell marker CD105. The terms "CD105+" or "CD105 positive" can also be used for a cell population comprising different cell types, if preferably at least 50, 60, 70, 80, 90, 95, 98 or 99 percent of the cell population express the cell marker CD105.

The term "CD105–" or "CD105 negative" as used herein refers to a cell not expressing the cell marker CD105. The terms "CD105–" or "CD105 negative" can also be used for a cell population comprising different cell types, if preferably less than 50% or at most 49, 40, 30, 20, 10, 5, 4, 3, 2, 1 or 0 percent of the cell population express the cell marker CD105.

The term "aSMA+" or "aSMA positive" as used herein refers to a cell expressing the cell marker aSMA. The terms "aSMA+" or "aSMA positive" can also be used for a cell population comprising different cell types, if preferably at least 50, 60, 70, 80, 90, 95, 98 or 99 percent of the cell population express the cell marker aSMA.

The term "aSMA–" or "aSMA negative" as used herein refers to a cell not expressing the cell marker aSMA. The terms "aSMA–" or "aSMA negative" can also be used for a cell population comprising different cell types, if preferably less than 50% or at most 49, 40, 30, 20, 10, 5, 4, 3, 2, 1 or 0 percent of the cell population express the cell marker aSMA.

The term "desmin positive" or "desmin+" as used herein refers to a cell expressing the cell marker desmin. The term "desmin positive" can also be used for a cell population comprising different cell types, if preferably at least 50, 60, 70, 80, 90, 95, 98 or 99 percent of the cell population express the cell marker desmin.

The term "desmin negative" or "desmin–" as used herein refers to a cell not expressing the cell marker desmin. The term "desmin negative" can also be used for a cell population comprising different cell types, if preferably less than 50% or at most 49, 40, 30, 20, 10, 5, 4, 3, 2, 1 or 0 percent of the cell population express the cell marker desmin.

The term "smoothelin positive" or "smoothelin+" as used herein refers to a cell expressing the cell marker smoothelin. The term "smoothelin positive" can also be used for a cell population comprising different cell types, if preferably at least 50, 60, 70, 80, 90, 95, 98 or 99 percent of the cell population express the cell marker smoothelin.

The term "smoothelin negative" or "smoothelin–" as used herein refers to a cell not expressing the cell marker smoothelin. The term "smoothelin negative" can also be used for a cell population comprising different cell types, if preferably less than 50% or at most 49, 40, 30, 20, 10, 5, 4, 3, 2, 1 or 0 percent of the cell population express the cell marker smoothelin.

The term "fusion competent" or "skeletal-myogenic" as used herein refers to cells able to fuse to multinucleated myotubes with at least 50, 60, 70, 80, 90 or 100 percent of nuclei within multinucleated myotubes following cultivation in skeletal muscle differentiation media for 5-7 days.

The term "non-fusion competent" or "non-skeletal-myogenic" as used herein refers to cells not able to fuse to multinucleated myotubes with less than 50% or at most 49, 30, 20, 10 or 0 percent of nuclei within multinucleated myotubes following cultivation in skeletal muscle differentiation media for 5-7 days.

The term "skeletal muscle differentiation media" as used herein refers to cell culture media which induce fusion in multinucleated fusion competent cells or myogenic cells as e.g. myoblasts. However, said term refers also to cell culture medium not comprising any substances necessary for the induction of fusion, in case the multinucleated fusion competent cells or myogenic cells are able to fuse without a respective induction.

The term "smooth muscle differentiation media" as used herein refers to cell culture media which induce transdifferentiation of cells to a smooth muscle phenotype. However, said term refers also to cell culture medium not comprising any substances necessary for the induction of transdifferentiation, in case cells are able to transdifferentiate without a respective induction.

The term "cell growth medium" as used herein refers to any medium suitable for the incubation of mammalian cells such as SMDCs, which allows the attachment of said mammalian cells on the surface of an incubation container as well as their proliferation.

The term "contractile" as used herein refers to collagen gel lattice contraction of at least 40% from the initial gel size within 48 hours.

The term "non-contractile" as used herein refers to collagen gel lattice contraction of less than 40% from the initial gel size within 48 hours.

The term "TGF-beta" is used for the transforming growth factor beta which is a multifunctional cytokine belonging to the transforming growth factor superfamily that includes three different isoforms (TGF-β 1, 2 and 3) and many other signaling proteins produced by all white blood cell lineages. The term "TGF-beta" is used synonymously with the terms "TGF-β", "TGF-b", "TGFb" and "TGFB".

The term "AChE positive" or "AChE+" as used herein refers to an acetylcholinesterase enzymatic activity of at least $1*10^3$ mUrel per mg of cellular protein measured in cells that have been cultivated in smooth muscle differentiation medium as e.g. described in the examples herein. Alternatively, acetylcholinesterase enzymatic activity can be tested by any test known in the art as e.g. described in Thurner et al., 2018.

The term "AChE negative" or "AChE–" as used herein refers to an acetylcholinesterase enzymatic activity of less than $1*10^3$ mUrel per mg of cellular protein measured in cells that have been cultivated in smooth muscle differentiation medium as e.g. described in the examples herein. Alternatively, acetylcholinesterase enzymatic activity can be tested by any test known in the art as e.g. described in Thurner et al., 2018.

The term "CK positive" or "CK+" as used herein refers to a creatine kinase activity of at least $1*10^2 mU_{rel}$ per mg of cellular protein measured in cells that have been cultivated in smooth muscle differentiation medium as e.g. described in the examples herein. Alternatively, acetylcholinesterase enzymatic activity can be tested by any test known in the art as e.g. described in Thurner et al., 2018.

The term "CK negative" or "CK–" as used herein refers to an creatine kinase enzymatic activity of less than $1*10^2$ mUrel per mg of cellular protein measured in cells that have been cultivated in smooth muscle differentiation medium as e.g. described in the examples herein. Alternatively, creatine kinase activity can be tested by any test known in the art as e.g. described in or as a skilled person in the art would conduct the analysis (Thurner et al. 2018).

The term "CD49e+" or "CD49 positive" as used herein refers to a cell expressing the cell marker CD49e. The terms "CD49e+" or "CD49e positive" can also be used for a cell population comprising different cell types, if preferably at least 50, 60, 70, 80, 90, 95, 98 or 99 percent of the cell population express the cell marker CD49e.

The term "CD49e–" or "CD49e negative" as used herein refers to a cell not expressing the cell marker CD49e. The terms "CD49e–" or "CD49e negative" can also be used for a cell population comprising different cell types, if preferably less than 50% or at most 49, 40, 30, 20, 10, 5, 4, 3, 2, 1 or 0 percent of the cell population express the cell marker CD49e.

The term "Pax-7+" or "Pax-7 positive" as used herein refers to a cell expressing the transcription factor Pax-7. The terms "Pax-7+" or "Pax-7 positive" can also be used for a cell population comprising different cell types, if preferably at least 50, 60, 70, 80, 90, 95, 98 or 99 percent of the cell population express the cell marker Pax-7.

The term "Pax-7–" or "Pax-7 negative" as used herein refers to a cell not expressing the cell marker Pax-7. The terms "Pax-7–" or "Pax-7 negative" can also be used for a cell population comprising different cell types, if preferably less than 50% or at most 49, 40, 30, 20, 10, 5, 4, 3, 2, 1 or 0 percent of the cell population express the cell marker Pax-7.

The term "SSEA4+" or "SSEA4 positive" as used herein refers to a cell expressing the cell surface marker SSEA4. The terms "SSEA4+" or "SSEA4 positive" can also be used for a cell population comprising different cell types, if preferably at least 50, 60, 70, 80, 90, 95, 98 or 99 percent of the cell population express the cell marker SSEA4.

The term "SSEA4–" or "SSEA4 negative" as used herein refers to a cell not expressing the cell surface marker SSEA4. The terms "SSEA4–" or "SSEA4 negative" can also be used for a cell population comprising different cell types, if preferably less than 50% or at most 49, 40, 30, 20, 10, 5, 4, 3, 2, 1 or 0 percent of the cell population express the cell marker SSEA4.

The term "MPC" or "MPCs" as used herein refers to myogenic progenitor cells. In particular, the term "MPC" refers to myogenic progenitor cells which are characterized by a negative expression of aSMA, CD49a, and CD146. MPCs are skeletal-myogenic and not multipotent. MPCs may be further characterized by a positive expression of CD105, CD90, CD73, CD56, desmin, ACHE and/or CK and/or a negative expression of CD34. An example of properties of MPCs is shown in FIG. 15.

The term "MSC" or "MSCs" as used herein refers to mesenchymal stromal cells. In particular, the term "MSC" or "MSCs" refers to mesenchymal stromal cells which are characterized by a negative expression of aSMA, CD49a, and CD146. MSCs are non-fusion competent and non-skeletal-myogenic but multipotent. MSCs may be further characterized by a positive expression of CD105, CD90, CD73 and/or desmin and/or a negative expression of CD56, CD34, desmin, ACHE and/or CK. An example of properties of MSCs is shown in FIG. 15.

In accordance with the present invention, methods for obtaining induced smooth muscle cells (iSMCs) from skeletal muscle derived cells (SMDCs) are provided.

Skeletal Muscle Cell Derived Induced Smooth Muscle Cells

A first subject-matter of the present invention is directed to a method for obtaining induced smooth muscle cells (iSMCs), the method comprising the steps of: (a) obtaining skeletal muscle derived cells from a subject; (b) transdifferentiating skeletal muscle derived cells by cultivating the cells in a medium containing TGF-beta, in particular TGFb1, TGFb2 and/or TGFb3, and heparin to obtain iSMCs. In a particularly preferred embodiment the skeletal muscle derived cells are transdifferentiated in step (b) by cultivating the cells in a medium containing TGFb1 and/or TGFb3, more preferably TGFb1, and heparin to obtain iSMCs. Step (b) of the present invention is performed in vitro or ex vivo. Accordingly, the method according to the present invention is an in vitro or ex vivo.

In a preferred embodiment of the present invention, step (b) is conducted in a cell culture medium containing 1-10 μg/ml TGFb1 and 10-30 μg/ml Heparin or 1-6 U/ml Heparin.

In a preferred embodiment the iSMCs obtained according to a method of the present invention, preferably in step (b) of the method according to the present invention, are characterized by the positive expression of aSMA, CD49a, and CD146.

In a preferred embodiment of the present invention, the skeletal muscle derived cells are myogenic progenitor cells (MPCs) characterized by the positive expression of CD56 and desmin, and the negative expression of CD34; alternatively, the skeletal muscle derived cells are mesenchymal stromal cells (MSCs) characterized by the positive expression of CD105, CD73, and the negative expression of CD34, and CD56.

In a preferred embodiment of the invention, the skeletal muscle derived cells are oligopotent MPCs.

In a further preferred embodiment of the present invention, the skeletal muscle derived cells are MSCs characterized by the negative expression of desmin and/or the positive expression of CD90.

In a further preferred embodiment of the present invention, the skeletal muscle derived cells are multipotent MSCs.

Preferably, in the method according to the present invention it is foreseen that the iSMCs obtained from MPCs in step (b) are characterized by the positive expression of aSMA, CD49a, desmin, CD56, and CD146, and the negative expression of CD34; and foresees that the iSMCs obtained from MSCs in step (b) are characterized by the positive expression of aSMA, CD49a and CD146, and the negative expression of CD56.

In a further preferred embodiment of the invention, the iSMCs obtained from MPCs in step (b) are further characterized by a positive expression of smoothelin.

In a further preferred embodiment of the present invention, the iSMCs obtained from MSCs in step (b) are further characterized by a negative expression of desmin and/or CD34.

CD73 or 5'-nucleotidase (5'-NT), also known as ecto-5'-nucleotidase, is an enzyme that in humans is encoded by the NT5E gene. CD73 commonly serves to convert AMP to adenosine. CD73 is expressed on lymphocytes, fibroblasts, smooth muscle cells, endothelial cells and myoblast. CD73 is a multipotent mesenchymal stromal cell (MSCs) marker according the minimal criteria for MSCs as suggested by the international society for cellular therapy (ISCT) (Dominici et al., 2006).

CD105 is also known as Endoglin. It is a type I integral membrane homodimer protein with subunits of 90 kD found on vascular endothelial cells and syncytiotrophoblasts of placenta. CD105 is weakly expressed on stromal fibroblasts. It is also expressed on activated monocytes and tissue macrophages. Expression of CD105 is increased on activated endothelium in tissues undergoing angiogenesis, such as in tumors, or in cases of wound healing or dermal inflammation. CD105 is a component of the TGF-β receptor system in human umbilical vein endothelial cells and binds TGF-β1 and β3 with high affinity. CD105 is a multipotent mesenchymal stromal cell (MSC) marker according the minimal criteria for MSC as suggested by the international society for cellular therapy (ISCT)(Dominici et al., 2006). As the present invention foresees the isolation of iSMCs from MPCs and/or MSCs by the incubation of the latter with TGFb, CD105 expression due to its role as a TGFb co-receptor can be helpful for the success of the method described herein. The present invention thus, discloses isolation of MSCs or MPCs (Example 1) that are CD105 positive (FIG. 2) and therefore useful for isolation of iSMCs (Example 2).

CD34 expression was described in muscle derived stem cells and quiescent satellite cells (Qu-Petersen et al., 2002). Further, CD34 positive skeletal muscle derived cells displayed enhanced regeneration of dystrophin in dystrophic skeletal muscle (Jankowski et al., 2002). State of the art is the use of CD34+ skeletal muscle derived cells for generation of smooth muscle cells in vitro and the use of CD34+ skeletal muscle derived cells for smooth muscle augmentation (Capelli et al., 2002). However, normal endogenous smooth muscles are generally CD34 negative (https://www.proteinatlas.org/ENSG00000174059-CD34/tissue/primary+data) but smooth muscles in a tumorigenic status frequently become CD34+(van de Rijn et al., 1994). Thus, cells obtained by the methods of the present invention lacking CD34 might be advantageous for smooth muscle regeneration and less prone to malignant transformation. Following the methods of the present invention, CD34 negative skeletal muscle derived cells are obtained in a first step and differentiated to CD34 negative iSMCs in a second step (Examples 1 and 2).

Figure 2:
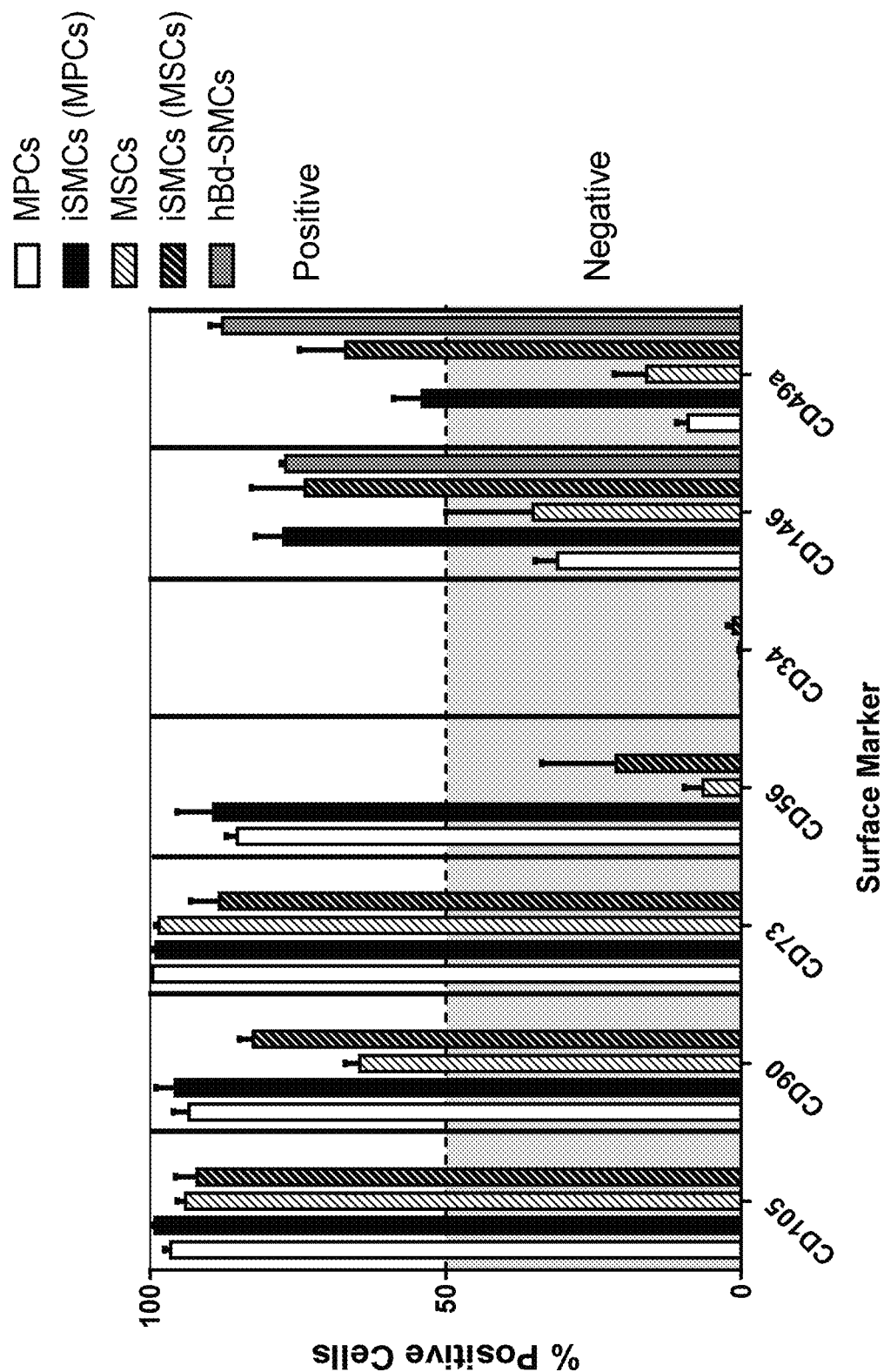

CD146 is a surface protein and receptor of laminin alpha 4, which is present in the extracellular matrix of developing smooth muscle tissue (Iivanainen et al., 1995). Further, CD146 was shown to be expressed in bone marrow derived stem cells committed to the smooth muscle lineage (Espagnolle et al., 2014). As depicted in FIG. 2, bladder derived smooth muscle cells are positive for CD146. Summarizing CD146+ cells mark a population of smooth muscle committed cells as preferred for the use of smooth muscle regeneration and or tissue engineering. The present methods allow isolation of CD146+ iSMCs from skeletal muscle derived cells.

CD56 also known as neural cell adhesion molecule (NCAM) is a myogenic commitment marker expressed in skeletal muscle myoblasts in vitro (Belles-Isles et al., 1993) and smooth muscle tissue in vivo (Romanska et al., 1996). CD56 is present in fusion competent desmin+ SMDC (herein termed MPCs) as well iSMCs originating from the latter. CD56 is the main discrimination marker between MPCs and the herein described skeletal muscle derived MSCs as both MSCs and the iSMCs originating from the latter are CD56 negative. CD56+ iSMCs as obtained by the present invention might be most suitable for smooth muscle regeneration.

Alpha smooth muscle actin (aSMA) is one of the first markers for smooth muscle commitment during development (McHugh, 1995). Its presence is essential for the function and contractility due to mechanotransduction in smooth muscle cells (J. Wang et al., 2006). Thus, the use of aSMA as a marker for iSMCs, intended for the regeneration of smooth muscle function, is essential. The present methods (Example 2) allow generation of aSMA+ cells from skeletal muscle derived cells (FIG. 3).

Desmin is one of the earliest known myogenic markers present in all muscle types. Lack of desmin can result in muscle degeneration and malfunction (Capetanaki et al., 1997). Thus, the use of desmin+ cells for muscle regeneration is to be preferred. As it is shown in FIG. 3, iSMCs derived from MPCs are desmin positive.

CD49a or integrin alpha protein (also VLA-1), resulting from expression and translation of the ITGA1 gene is present during smooth muscle development especially found in smooth muscle tissue such as the aorta (Belkin et al., 1990). The present methods allow isolation of CD49a positive iSMCs from CD49a negative MPCs or MSCs. As depicted in FIG. 2, human bladder derived smooth muscle cells (hBd-SMCs) are also positive for CD49a.

Functionality of smooth muscle tissue relies on the existence of highly differentiated smooth muscle cells expressing contractile proteins such as smoothelin (Niessen et al., 2005). Further, smoothelin is a well-known marker for fully differentiated smooth muscle cells and is the first marker to disappear when smooth muscle is compromised (van Eys et al., 2007). Thus, the use of smoothelin+ cells in regeneration of smooth muscle tissue might be favorable. Present methods (Example 2 and 5) allow isolation of smoothelin+ iSMCs from smoothelin-MPCs (FIG. 3).

As above described, mentioned markers CD146, CD56, aSMA, CD34, desmin, CD49a, smoothelin are important for the identification and/or function of smooth muscle cells, combination of the markers might be favorable to identify iSMCs suitable for smooth muscle regeneration. The herein demonstrated methods allow isolation of iSMCs with combinations of the addressed markers (Example 2).

In detail, the present invention provides a method to obtain iSMCs from skeletal muscle derived MPCs. The iSMCs obtained from MPCs are CD56+, aSMA+, CD49a+, desmin+, CD146+ and CD34−. The latter markers as described above are advantageous to identify smooth muscle cells, as for example hBd-SMCs are positive for CD146 and CD49a (FIG. 2) and thus are preferred for cells used as smooth muscle regenerating cells. The combination of CD56+, aSMA+, CD49a+, desmin+, CD146+ and CD34− marker expression is advantageous and novel for in vitro generated iSMCs from human skeletal muscle derived MPCs.

Further, the present invention provides a method to obtain iSMCs from skeletal muscle derived MSCs. iSMCs derived from skeletal muscle MSCs are aSMA+, CD146+CD49a+, CD56−, and preferably also desmin− and/or CD34−. The positive expression of aSMA, CD49a and CD146 and negative expression of CD56 and preferably also of CD34 is suitable to identify these cells as MSC derived smooth muscle cells and is relevant for the function of iSMCs as smooth muscle regenerating cells. The combination of aSMA+, CD146+, CD49a+ and CD56− marker expression on iSMCs from skeletal muscle derived MSCs is advantageous and novel over previous methods in the art.

In a further preferred embodiment of the present invention, the method comprises that after step (a) a step (a1) is conducted comprising proliferating the skeletal muscle derived cells, preferably to receive $20-40 \times 10^6$ cells.

In a particular preferred embodiment of the present invention, the skeletal muscle derived cells are proliferated to receive $50 \times 10^6$ cells.

In a further preferred embodiment of the present invention, step (b) is conducted for one to six days. In a particular preferred embodiment of the present invention, step (b) is conducted three to six days.

A further subject-matter of the present invention is directed to induced smooth muscle cells (iSMCs) obtained by a method according to the present invention.

In a further preferred embodiment of the present invention, the induced smooth muscle cells (iSMCs) obtained from MPCs are characterized by the positive expression of aSMA, CD49a, desmin, CD56, and CD146, and the negative expression of CD34.

As already enlightened above, the combination of markers present, aSMA, CD49a, desmin, CD56 and CD146, or absent, CD34, in iSMCs from MPCs are advantageous due to pheno-copying the natural expression profile of smooth muscle cells by the methods described herein.

In a further preferred embodiment of the present invention, the induced smooth muscle cells (iSMCs) obtained from MPCs are non-fusion competent.

Fusion of single nucleated myogenic progenitor cells (MPCs) or other fusion competent muscle derived cells (e.g. myoblasts) to multinucleated myotubes is a prerequisite for skeletal muscle formation and regeneration (Rochlin et al., 2010). However, as smooth muscle tissue in vivo does not consist of multinucleated myotubes but rather differentiated single nucleated smooth muscle cells, for the regeneration of smooth muscle non-fusion competent cells are of advantage. Thus, the present invention foresees that iSMCs from MPCs as well as iSMCs from MSCs are non-fusion competent. Whereas MPCs obtained as shown in Example 1 of the present invention, are fusion competent, iSMCs, obtained as shown in example 2 of the present invention and ultimately intended for application into smooth muscle tissue, are non-fusion competent. This applies both to MPC-iSMCs and to MSC-iSMCs according to the present invention as e.g. shown in FIG. 15.

In a further preferred embodiment of the present invention, the induced smooth muscle cells (iSMCs) obtained from MSCs are characterized by the positive expression of aSMA, CD49a, and CD146, and the negative expression of CD56.

Preferably, the iSMCs obtained from MSCs are further characterized by the negative expression of desmin and/or CD34.

As skeletal muscle derived MSCs are different from MPCs in terms of CD56 also iSMCs derived from MSCs are CD56 negative. However, MSCs derived iSMCs are aSMA+, CD146+ and CD34−, which in line with MPCs-derived iSMCs is representative for the smooth muscle commitment of MSCs derived iSMCs and thus advantageous. Further the expression of the mesenchymal markers CD90, CD105, CD73 positive in iSMCs derived from MSCs by the present invention is preferable due to the mesenchymal nature of the smooth muscle tissue in need.

The expression of the various markers as described above is preferably tested in vitro. Moreover, the expression of the various markers as defined above refers to their expression in the respective cells in vitro. In a preferred embodiment the in vitro expression of aSMA and desmin in the respective cells as defined above corresponds to their respective in vivo expression Preferably, the induced smooth muscle cells (iSMCs) express functional calcium and/or potassium channels.

Functionality of smooth muscle tissue relies on the existence functional voltage gated calcium and potassium channels, enabling the induction of regulated cell contraction and regulating membrane potential, respectively (Sanders, 2008). Upon neurologic stimulation, smooth muscle cell membranes depolarize which triggers voltage sensing calcium channels to open and enable calcium ions to enter the cell from the intercellular space (Sanders, 2008). This event in the following triggers signaling cascades ultimately leading to the actin/myosin induced contraction of the smooth muscle cell required in detail for the function of e.g. the internal anal sphincter to contract and hold liquids, gas and solids from involuntary release from the rectum (Webb, 2003). Further, the voltage gated potassium channels open after neuronal induced depolarization of the smooth muscle membrane in order to repolarize the membrane to allow further depolarizations in case of following neuronal signals. Thus, the presence of Calcium and Potassium channels on iSMCs is suitable to identify functional iSMCs in vitro. Functional iSMCs in fact are necessary to regenerate the malfunction of e.g. the internal anal sphincter not sufficiently functional in fecal incontinent patients. The present invention allows generation of iSMCs from skeletal muscle derived cells with both functional voltage gated potassium and calcium channels, which might be advantageous for their use in smooth muscle regeneration.

Preferably, the induced smooth muscle cells (iSMCs) are contractile in vitro. One of the typical functions of smooth muscle tissue is contraction (Webb, 2003). In order to test contractility in vitro, cells are seeded on collagen gel and the reduction in size of the collagen gel over time is quantified as a measure of contractility. The inventors found that iSMCs from MPCs and iSMCs from MSCs are contractile, compared to MPCs and MSCs originating thereof.

Preferably, the induced smooth muscle cells (iSMCs), in particular the MPC-iSMCs, obtained according to a method of the present invention, preferably in step (b), are CD49e−. CD49e expression is preferably tested in vitro. CD49e, also known as integrin alpha 5, is a cell adhesion molecule, which builds a heterodimer receptor with integrin beta 1 for binding fibronectin, fibrinogen and fibrillin-1. As fibronectin inhibitors were sufficient to increase smooth muscle gene expression, fibronectin signaling supported via CD49e might hinder expression of smooth muscle. The inventors found that iSMCs from murine MPCs are deficient of CD49e. Deficiency in CD49e might be helpful in reducing fibronectin signaling and thus CD49e− iSMCs obtained according to the present invention could be advantageous over cells known in the art in their use for smooth muscle regeneration.

In an alternative preferred embodiment, the induced smooth muscle cells (iSMCs), in particular the MPC-iSMCs, obtained according to a method of the present invention, preferably in step (b), are CD49e+. CD49e expression is preferably tested in vitro.

Preferably, the induced smooth muscle cells (iSMCs), in particular the MPC-iSMCs, obtained according to a method of the present invention, preferably in step (b), are AChE−. AChE expression is preferably tested in vitro. One of the typical functions of skeletal myogenic cells is the expression of active AChE enzyme during in vitro fusion (Thurner et al., 2018) as is necessary for termination of nerve signals at motoric endplates. However, smooth muscle is not innervated by motoric neurons and thus its contraction is not majorly regulated by Acetylcholine, requiring AChE for termination. The inventors have analyzed iSMCs isolated according to Example 3 for AChE activity according to Example 17 and found that iSMCs are AChE−(FIG. 14).

Preferably, the induced smooth muscle cells (iSMCs), in particular the MPC-iSMCs, obtained according to a method of the present invention, preferably in step (b), are CK−. CK expression is preferably tested in vitro. One of the typical function of skeletal myogenic cells is the expression of active CK enzyme during in vitro fusion (Thurner et al., 2018) as it is necessary for skeletal muscle contraction. However, smooth muscle contraction is not regulated by creatine kinase (CK) and thus not necessary for smooth muscle cells. The inventors found that iSMCs (Example 3), which were analyzed for CK activity (Example 17), are CK−(FIG. 14).

In a preferred embodiment, the induced smooth muscle cells (iSMCs), in particular the MPC-iSMCs, obtained according to a method of the present invention, preferably in step (b), are Pax-7 negative, in particular if Pax-7 expression is tested in vitro. In a further preferred embodiment, the induced smooth muscle cells (iSMCs), in particular the MPC-iSMCs, obtained according to a method of the present invention, preferably in step (b), are Pax-7 positive, in particular if Pax-7 expression is tested in vitro. Pax-7 is a transcription factor found in cells committed to the skeletal muscle lineage (Krauss et al., 2016). Deletion of Pax-7 in the tunica muscularis of mice leads to a reduction in skeletal muscle and increase in smooth muscle mass (Worl et al., 2009).

In a preferred embodiment the induced smooth muscle cells (iSMCs), in particular the MPC− iSMCs, obtained according to a method of the present invention, preferably in step (b), are SSEA4 negative. In a further preferred embodiment the induced smooth muscle cells (iSMCs), in particular the MPC-iSMCs, obtained according to a method of the present invention, preferably in step (b), are SSEA4 positive. SSEA4 expression is preferably tested in vitro. SSEA4 is a cell surface marker found in pluripotent stem cells, which are known for their extensive proliferative potential and thus pose the risk of tumorigenesis.

Induced Smooth Muscle Cell Based Treatments

A further subject-matter of the present invention is directed to induced smooth muscle cells (iSMCs) for use in a method of treating a disease or disorder in a subject.

Preferably, the subject is a human or an animal. In particular, the present invention provides induced smooth muscle cells (iSMCs) for use in a method for treatment of the human or animal body by surgery or therapy. More particularly, the present invention provides induced smooth muscle cells (iSMCs) for use in cell therapy, in particular in smooth muscle cell therapy.

In a further preferred embodiment of the present invention, the disease or disorder are smooth muscle deficiencies. Preferably the smooth muscle deficiencies are selected from the group consisting of anal incontinence, urinary incontinence, reflux disease, gastroparesis, overactive and underactive bladder.

In a specifically preferred embodiment of the present invention, the disease or disorder is fecal incontinence, in particular passive fecal incontinence. Accordingly, the present invention also refers to iSMCs for use in a method of treating anal incontinence, urinary incontinence, reflux disease, gastroparesis, overactive and underactive bladder, and in particular of fecal incontinence, more particularly passive fecal incontinence.

Preferably the iSMCs are injected into smooth muscle tissue of a subject in need of iSMCs. Preferably, the iSMCs are injected in an amount effective for treating the smooth muscle deficiency. The effective amount of the compound to be administered can be readily determined by those skilled in the art during pre-clinical trials and clinical trials by methods familiar to physicians and clinicians.

Regeneration of smooth muscle tissue in need such as weakened, atrophic or damaged smooth muscle e.g. sphincters such as the internal anal, internal urethral, lower or upper esophageal sphincters by cell administration requires cells to be locally administered into the tissue in need. Local administration of the iSMCs might regenerate smooth muscle by engraftment of injected iSMCs at the site of administration. Previous art (Chancellor et al., 2001) discloses skeletal muscle derived cells characterized as desmin+, CD34+ and Blc-2+ and their use in augmenting soft tissue (e.g. smooth muscle) such as of the bladder or anal sphincter. In contrast, the present invention discloses the isolation of CD34−, CD56+, desmin+ MPCs or multipotent, CD34−, CD56−, CD73+ and CD105+ MSCs skeletal muscle derived cells in a first step. From said cells of the skeletal muscle, iSMCs can be isolated in a second step, following treatment with TGFb1 and heparin. These iSMCs thereby gain a smooth muscle phenotype by expression of smooth muscle marker such as e.g. aSMA and CD146 and thus can be of advantage for smooth muscle regeneration. Preferably these iSMCs are used in a method to treat a subject in need by injection into said subject. The inventors found that, iSMCs obtained by the methods of the present invention being administered into the smooth muscle tissue of the pyloric sphincter, engrafted at the site of injection and integrated into the smooth muscle tissue.

Preferably iSMCs are administered into a soft tissue in need by multiple injections.

Multiple injections of SMDCs into skeletal muscle have shown to improve the engraftment of cells into the muscle (Skuk et al., 2014). The present invention foresees the injection of iSMCs into soft tissue such as e.g. smooth muscle at multiple sites of the same continuum of tissue. In particular, cells might be administered using multiple needles, each injecting a defined number of cells.

The iSMCs according to the present invention may be administered in form of a pharmaceutical composition comprising the iSMCs and a pharmaceutically acceptable diluent, excipient or carrier. Accordingly, the present invention also refers to a pharmaceutical composition comprising iSMCs according to the present invention and a pharmaceutically acceptable diluent, excipient or carrier.

In another embodiment of the present invention iSMCs are used in the manufacture of a medicament for the treatment of anal incontinence, urinary incontinence, reflux disease, gastroparesis, overactive and underactive bladder, and in particular of fecal incontinence, more particularly passive fecal incontinence.

Tissue Engineering

In a further subject-matter of the present invention, induced smooth muscle derived cells are for use in tissue engineering.

Smooth muscle tissue often forms ring/tube shaped structures within the human body, such as blood vessels and the internal anal sphincter. The use of iSMCs as obtained herein to produce ring/tube shaped structures can be used for the in vitro engineering of blood vessels or sphincter muscles. In vitro engineered smooth muscle structures can be of use to replace malfunctioned smooth muscle structures such as smooth muscle sphincters in e.g. fecal incontinent patients. The inventors found that iSMCs obtained by the present invention can rebuild ring-shaped three-dimensional structures similar to that of e.g. the internal anal sphincter. Cells within these tissue rings were found to express smooth muscle marker proteins such as aSMA and desmin. The expression of contractile proteins aSMA and desmin within tissue rings obtained by the cells of the present invention is required for the functionality of the tissue rings and thus is of advantage for the use of said tissue rings in tissue replacement.

Additionally, iSMCs derived in vitro engineered sphincters were found herein to harbor ultrastructural properties of natural smooth muscles such as highly abundant actin structures and dense bodies necessary for mechanotransduction and thus functionality of smooth muscle constructs. Further, tissue engineered sphincters obtained by the present invention allow formation of calveolae within the cells. Calveolae are known to be of necessity for calcium handling e.g. by excitation-contraction, excitation-transcription and pharmacomechanical coupling (Popescu et al., 2006). Therefore, iSMCs as obtained by the present invention are promising for the use in tissue engineering.

Drug Screening

In a further subject-matter of the present invention, iSMCs are for use in drug screening. The use of iSMCs to produce smooth muscle structures in vitro might be of use to test novel drugs and their effects on smooth muscle cells in vitro before any potentially harmful drug candidate has to be used in animal or human studies.

Skeletal Muscle Derived Cells for Generation of Induced Smooth Muscle Cells

A further subject-matter of the present invention is directed to the use of skeletal muscle derived cells for obtaining induced smooth muscle cells (iSMCs).

Frequently used state of the art methods use induced pluripotent stem cells (Dash et al., 2016), adipose derived multipotent mesenchymal stromal cells (G. Wang et al., 2015) or bone marrow derived multipotent mesenchymal stromal cells (Espagnolle et al., 2014) in order to obtain smooth muscle cells in vitro, which are clearly different in origin to the skeletal muscle derived cells used as a source to obtain induced smooth muscle cells in the present invention. The disadvantage of current state of the art cells e.g. iPSCs used to obtain smooth muscle cells is the risk of malign transformation due to the genetic engineering necessary to obtain iPSCs. Another state of the art method describes CD34+ skeletal muscle derived cells as a source for smooth muscle cells. Thereby said cells are cultivated in a differentiation medium for 2-4 weeks (Lu et al., 2011). Within the present invention for the first time, CD34− skeletal muscle derived cells isolated according to the methods of the present invention are used to obtain iSMCs. Said skeletal muscle derived cells are suited well for isolation of iSMCs as the method of the present invention takes less than 1 week.

In a preferred embodiment according to the present invention, the skeletal muscle derived cells are oligopotent myogenic progenitor cells (MPCs) characterized by the positive expression of CD56, and desmin, and the negative expression of CD34; or wherein the skeletal muscle derived cells are multipotent mesenchymal stromal cells (MSCs) characterized by the positive expression of CD105, CD73, and the negative expression of CD34 and CD56.

The following examples explain the present invention but are not considered to be limiting.

EXAMPLES

Example 1—Isolation of Skeletal Muscle Derived Cells (SMDCs)

Depending on the following isolation methods, SMDCs were either enriched for human myogenic progenitor cells (MPCs), murine myogenic progenitor cells (mMPCs) or human multipotent mesenchymal stromal cells (MSCs).

Isolation of Human Skeletal Muscle Derived Myogenic Progenitor Cells (MPCs)

In detail, a skeletal muscle biopsy was taken from *M. pectoralis major* or *M. biceps brachii* of an incontinent patient. In order to take the biopsy, first the skin was opened by an approximately 1 cm long incision above the muscle until the fascia of the *M. pectoralis major* was reached. After opening of the fascia, 1 cm³ of muscle tissue (biopsy) was taken. The biopsy was directly transferred into a biopsy transportation medium precooled to approximately 4° C. and comprised of Ham's F10 basal medium supplemented with Gentamicin (1-5 µg/ml final concentration). The biopsy was stored for approximately 26 hours at 1-11° C. within the biopsy transportation medium. Next, the biopsy was transferred to a petri dish filled with 1×PBS. The muscle tissue was separated from connective tissue using sterile forceps and a scalpel. Then, the muscle tissue was transferred into another petri dish filled with 1×PBS and dissected into 2-3 mm² sized pieces using a scalpel. After an additional transfer step as above the tissue pieces were further cut into 1 mm pieces. The pieces finally were transferred into a centrifugation tube filled with 1×PBS and centrifuged for 10 minutes at 1300 rpm. After centrifugation the supernatant was removed and the muscle tissue resuspended in 1×PBS supplemented with 8 µg/ml Gentamicin. The muscle tissue suspension then was cooled to 2-8° C. for 48 hours. After the cooling the muscle tissue suspension was centrifuged for 10 minutes at 1300 rpm, the supernatant was then removed and 2.5 ml of a digestion solution containing 1-5 mg/ml collagenase, 2-4% v/v Hepes buffer, 0.1-10% v/v fetal calf serum and 5-10 µg/ml Gentamicin in Ham's F10. The muscle tissue suspension then was incubated for 6 to 20 hours at 37° C., 5% $CO_2$. Next, the suspension was centrifuged at 1300 rpm for 10 minutes, the supernatant was removed, the pellet resuspended in medium containing 10-20% v/v FCS, 1-3 ng/ml bFGF and 3-10 µg/ml Gentamicin in Hams F10 and plated on cell culture flasks. SMDCs attached to the bottom of the culture flask were further maintained by changing medium every 3-4 days and sub cultivation following detachment after confluency was reached. Sub-cultivation was performed until $1\times10^7$ to $5\times10^7$ SMDCs were reached.

Isolation of Murine Skeletal Muscle Derived Myogenic Progenitor Cells (mMPCs)

Murine MPCs were obtained from skeletal muscle biopsies of Gt(ROSA)26Sortm4(ACTB-tdTomato,-EGFP)Luo/J, in short TdTomato mice, (Jackson Laboratory, Maine, USA). Adult mice were sacrificed by cervical dislocation followed by pinching the skin on the back and peeling off the skin. Next, skeletal muscle was obtained from longissimus dorsi, gastrocnemius and tibialis anterior muscles using scissors and scalpel. The muscles were transferred into a sterile petri dish and covered with 1×PBS. Then, using tweezers and a scalpel, the remaining connective tissue was removed from skeletal muscle and discarded. Afterwards, the muscle tissue was digested using the skeletal muscle dissociation kit (MiltenyiBiotec GmbH, Bergisch Gladbach, Germany) following manufacturer's instructions. In order to separate myogenic progenitor cells (mMPCs) from non-myogenic SMDCs, a satellite cell isolation kit (Miltenyi Biotec, Bergisch Gladbach, Germany) was used according to the manufacturer's instructions. Collected mMPCs and non-myogenic SMDCs were centrifuged as above and resuspended in mouse growth medium, consisting of DMEM/Ham's F12 supplemented with 20% FCS and bFGF. Murine SMDCs were cultivated on collagen coated culture flasks, prepared by covering the surface of culture flasks with collagen I from rat tail diluted 1:10 1×PBS for 1 hour at 37° C. Sub cultivations were performed like for human SMDCs. Finally cells were detached from the walls of the cell culture vessel resuspended in medium and used immediately or cryopreserved in liquid nitrogen until further use.

Isolation of Human Skeletal Muscle Derived Multipotent Mesenchymal Stromal Cells (MSCs)

MSCs were isolated according to Thurner et al. 2018. First, SMDCs were isolated from muscle biopsies (*Musculus pectoralis* major or *Latissimus dorsi*) and expanded under a cGMP environment. Cells were maintained by standard cell culture methods. Briefly, cells were cultured in growth medium containing Ham's F-10 basal medium supplemented with 10% FCS (inactivated at 57° C., 40 minutes), bFGF and gentamicin and incubated at 37° C., 5% $CO_2$. Growth medium was changed every 2 to 3 days. For sub-cultivation and harvest, the cells were washed once with 1×PBS and incubated with 1× Trypsin solution for 5 minutes at 37° C. Cells were rinsed with growth medium and centrifuged at 400*g for 10 minutes, supernatant was discarded and the pellet resuspended in growth medium. Next, MSCs were purified by magnetic activated cell sorting (MACS). Therefore, human CD56 MicroBeads kit (MiltenyiBiotec GmbH, Bergisch Gladbach, Germany) was used. In summary, after harvesting and counting, the cells were centrifuged at 400*g for 10 minutes, supernatant was discarded and cells were resuspended in 10 mL of MACS-buffer. After another centrifugation step (400*g for 10 minutes), the pellet was resuspended in 80 µL MACS-buffer. Subsequently, 20 µL of magnetic CD56 antibody was added per $1*10^7$ cells and incubated for 15 minutes at 4° C. Afterwards, sorting of cells was carried out with Mini MACS Separator and CD56− MSCs were collected in the flow through. Finally cells were resuspended in medium and cryopreserved in liquid nitrogen until further use or used immediately.

Example 2—Transdifferentiation of SMDCs to iSMCs and Isolation Thereof

MPCs, murine MPCs or MSCs as obtained in Example 1, were seeded to the walls of a culture vessel and cultivated with growth medium to a confluency of about 70%. Then, cells were washed once with DMEM/F12 (Thermo Scientific, MA, USA). Next, cells were covered with smooth muscle differentiation medium, consisting of DMEM/F12 supplemented with recombinant human TGFb1 (Thermo Scientific, MA, USA), Heparin sodium salt from porcine intestinal mucosa (Sigma-Aldrich Co. LLC, MO, USA), heat inactivated (57° C., 40 minutes) fetal calf serum (Gibco, Thermo Scientific, MA, USA) and gentamicin (Sandoz GmbH, Tirol, Austria) to a final concentration of 10 ng/ml, 3.84 µg/ml and 5% (v/v), respectively. Finally, cells were cultivated in smooth muscle differentiation medium for 3-6 days at 37° C., 5% $CO_2$. Medium was changed every 3-4 days. For isolation, cells were detached from the walls of the culture vessels and collected in a suspension.

Example 3—Differentiation Potential of SMDCs

For adipogenic-, chondrogenic- and osteogenic differentiation in vitro, each 500 000 cells obtained by Example 1 were seeded onto 6-well plates (NUNC, Thermo Scientific, MA, USA) and cultivated in growth medium for 24 hours at 37° C., 5% $CO_2$. Next, cells were washed once with 5 ml DMEM/Ham's F12 and covered with each 5 ml adipogenic-, chondrogenic- or osteogenic differentiation medium. Adipogenic, chondrogenic and osteogenic differentiation medium consisted of StemXVivo™ Osteogenic/Adipogenic Base Medium (R&D Systems Inc., MN, USA, supplemented with StemXVivo Human/Mouse/Rat Adipogenic (R&D Systems Inc., MN, USA, StemXVivo Human Osteogenic Supplement (R&D Systems Inc., MN, USA, or STEMPro® Chondrogenesis Supplement (Gibco®, Thermo Scientific, MA, USA), respectively, according to the manufacturer's instructions. Differentiation media were further supplemented with gentamicin (Sandoz GmbH, Austria) to reach a final concentration of 3.83 µg/ml. Cells were cultivated each for 14 days in respective differentiation media, which was changed every 2-3 days. After 14 days of cultivation, successful differentiation was assessed by the presence of adipocytes, chondrocytes and osteocytes visualized by oil red o (adipocytes), alcian blue (chondrocytes) and alizarin red s (osteocytes) staining, respectively. Quantification of oil red o, alcian blue and alizarin red s staining was performed on microscopic images of multiple individual experiments by image j software package. Therefore, images were loaded and color channels split. Red channels were used for oil red o and alizarin red s stainings, while blue channel was used for alcian blue stainings. Background was eliminated by setting a common threshold and average pixel intensity per field was acquired for quantification by image j. Statistical comparison was performed by unpaired t-test, considering a p<0.05 as significant (*). p<0.01, p<0.001 visualized as * or **, respectively. Skeletal muscle differentiation was initiated in cells culture in 24-well Nunclon™ Delta Surface plastic plates (Thermo Scientific, MA, USA) by replacing the growth medium with Skeletal Muscle Cell Differentiation medium (500 mL, PromoCell GmbH, Germany), supplemented with 10 mL of Skeletal Muscle Cell Differentiation Medium Supplement Pack (PromoCell GmbH, Germany) and 240 µL gentamicin (8 mg/mL, Sandoz GmbH, Austria) as described before (Thurner et al., 2018).

MPCs and MSCs obtained by Example 1 were tested for in vitro differentiation to adipogenic, chondrogenic, osteogenic and skeletal myogenic lineage under the appropriate culture conditions. Staining for adipocytes, chondrocytes, osteocytes and myotubes was carried out as described above. Oil red o and alizarin red s positive cells were absent within MPCs and only low levels of alcian blue cells could be detected. Within MSCs, cells positive for oil red o, alcian blue and alizarin red s were found following cultivation in adipogenic, chondrogenic and osteogenic differentiation medium, respectively (FIG. 1A, B) confirming their enrichment of multipotent cells and status of multipotent mesenchymal stromal cells as defined by the International Society for Cellular Therapy (Dominici et al., 2006). Only within MPCs desmin positive multinucleated myotubes were detected (FIG. 1A). Quantification of oil red o, alcian blue and alizarin red s staining intensities following adipogenic, chondrogenic and osteogenic differentiation in vitro, respectively, as well as fusion index calculation following skeletal myogenic differentiation of MSCs and MPCs, revealed a significantly higher staining intensity in oil red o (p=0.0117), alcian blue (p=0.0020) and alizarin red s (p=0.0012) staining of MSCs compared to MPCs, whereas a significantly higher fusion index (p=0.0007) was found within MPCs compared to MSCs (FIG. 1B). Thus, MPCs are mesenchymal oligopotent cells, committed to myogenic lineage. Moreover, MSCs are multipotent and capable of adipogenic-, chondrogenic- and osteogenic-differentiation in vitro.

Example 4—Surface Marker Expression

To determine surface marker expression, flow cytometry was performed on a Guava easyCyte 6HT 2L flow cytometer (Merck Millipore, Darmstadt, Germany). Briefly, cells obtained by Example 1 were harvested by covering with 1× trypsin at 37° C. for 5 minutes, centrifuged at 400*g and resuspended in 1×PBS supplemented with 1% FCS. 40 000 cells were resuspended in 195 µl 1×PBS and incubated after addition of 5 µL CD34-PE, CD56-PE, CD146-PE, IgG1-PE, IgG1-FITC, CD90-PE, CD105-PE, (all from Beckman Coulter, CA, USA), CD49a-FITC (Miltenyi Biotec, Germany) or CD73-PE (Becton Dickinson, NJ, USA) for 30 minutes in a 1.5 mL Eppendorf tube at 4° C. in dark. Next, cells were washed with 1 mL PBS, centrifuged at 400*g for 10 minutes and resuspended in 195 µL of 1×PBS in a 96-well round bottom plate. Then, each reaction received 5 µL of viability dye 7-aminoactinomycin D (Beckman Coulter Inc., France) and the plate was incubated for 10 minutes at RT in dark. Finally, cell events were acquired with Guava InCyte™ v.2.3 software. Histograms and dot-plots were generated with a minimum of 5000 events at a sample flow rate of 1.8 µL/mL. Positive staining was obtained by comparison with Isotype control set as at least 95% negative or comparison to control (negative) cells.

In order to characterize MPCs and MSCs at least 4 samples from individual patients obtained by methods used in Example 1 as well as iSMCs derived thereof by methods used in Example 2, were tested for the presence of mesenchymal lineage markers (CD105, CD90, and CD73), hematopoietic marker (CD34), myogenic marker (CD56) and smooth muscle lineage marker(CD146). A mean % positive cells of ≥50 was considered as positive whereas a mean of <50 was considered negative. Therefore, all cell types were found positive for CD105, CD90 and CD73 but were negative for CD34 (FIG. 2). Moreover MPCs and iSMCs derived thereof were CD56+ but MSCs and iSMCs derived thereof were CD56−.

Interestingly, the expression of the surface marker CD146, associated with the vascular smooth muscle commitment of MSCs (Espagnolle et al., 2014), and CD49a, expressed during smooth muscle development (Belkin et al., 1990), was negative in both MPCs and MSCs but positive in iSMCs derived thereof (FIG. 2).

Example 5—Intracellular Marker Expression

Immunofluorescence staining was performed to detect intracellular marker expression directly on gelatin coated 24-well plates or glass cover slips placed in 6-well plates as described before (Thurner et al., 2018). For fluorescent immunolabeling of alpha smooth muscle actin (aSMA), smoothelin, or desmin, cells were incubated with a mouse anti-actin alpha-smooth muscle (Sigma-Aldrich Co. LLC, MO, USA), mouse anti-smoothelin (Merck Millipore, MA, USA), anti-smooth muscle myosin heavy chain (Merck Millipore, MA, USA) or rabbit anti-desmin (Thermo Scientific, MA, USA) antibody, respectively, each diluted 1:100 in blocking medium, were used. Secondary goat anti-mouse Alexa488 or donkey anti-rabbit Alexa547 conjugated antibodies (Thermo Scientific, MA, USA), diluted 1:200 in blocking medium were used. Counterstaining of nuclei was performed by incubating the cells with Hoechst33342 (Sigma-Aldrich Co. LLC, MO, USA) diluted to a final concentration of 2 µg/mL in PBST (0.1% Triton X-100). Cells were mounted with Entellan® (Merck Millipore, MA, USA) and sealed with glass coverslips. Stainings were compared to (1) procedures without primary antibodies and (2) cells negative for tested antibodies. In order to quantify the number of positive cells, overlays of Hoechst and antibody stainings were performed and multiple images of at least three independent cell preparations were analyzed. The total number of cells positive for antibody staining was divided by the total number of cells (nuclei) as assessed with Hoechst staining. Mean and standard error values were calculated to compare cells obtained by Examples 1 and 2.

MPCs and MSCs obtained by Example 1 as well as iSMCs derived thereof as described in Example 2 were analyzed for the expression of intracellular contractile smooth muscle proteins (aSMA, Smoothelin) as well as the general myogenic marker desmin by fluorescent immunostaining. MPCs and MSCs were aSMA- and Smoothelin-. In contrast, iSMCs isolated from both, MSCs and MPCs were found aSMA+(FIG. 3). Further, iSMCs isolated from MPCs in Example 2 were found Smoothelin+. Analysis of intracellular Desmin expression revealed, that MSCs and iSMCs isolated thereof are Desmin-. In contrast, both MPCs and iSMCs isolated thereof are Desmin+(FIG. 3).

Example 6—Gene Expression

Total RNA of $1 \times 10^6$ MPCs or MSCs each obtained as shown in Example 1 and iSMCs derived thereof as shown in Example 2 was isolated by RNEasy Kit (QIAGEN, Hilden, Germany) according to the manufacturers' instructions. Sample preparation for microarray hybridization was carried out as described in the NuGEN Ovation PicoSL WTA System V2 and NUGEN Encore Biotin Module manuals (NuGEN Technologies, Inc, San Carlos, Calif., USA). Hybridized arrays were washed and stained in an Affymetrix Fluidics Station FS450, and the fluorescent signals were measured with an Affymetrix GeneChip Scanner 3000 7G. Fluidics and scan functions were controlled by the Affymetrix GeneChip Command Console v4.1.3 software. Sample processing was performed at an Affymetrix Service Provider and Core Facility, "KFB—Center of Excellence for Fluorescent Bioanalytics" (Regensburg, Germany)

Summarized probe set signals in log 2 scale were calculated by using the RMA algorithm with the Affymetrix GeneChip Expression Console v1.4 Probeset IDs with highest log 2 fold change between MPCs and MPCs-iSMCs were used for subsequent analysis and comparison to log 2 fold changes between MSCs and MSCs-iSMCs. Overview of all analyzed genes and the respective log 2 fold changes in between MSCs and MSCs-iSMCs as well as between MPCs and MPC-iSMCs is demonstrated in (FIG. 12). Log 2 fold changes ≥1 were considered to mark an upregulation and thus are marked with an asterisk (*). Heatmaps were generated with Multiple Expression Viewer (MeV 3.1.0) software in order to visualize log 2 fold changes and perform hierarchical clustering as well as k-means clustering according to Euclidean distance.

A microarray analysis was carried out to study changes in gene expression associated with isolation of the iSMCs in the present invention. Smoothelin (SMTN), calponin1 (CNN1), tropomyosin1 (TPM1), transgelin (TGLN, SM22), integrin-alpha-3 (ITGA3), integrin-alpha-1 (ITGA1, CD49a) vinculin (VCL) and melanoma cell adhesion molecule (MCAM, CD146) (Espagnolle et al., 2014; Miano, 2010; Xie et al., 2011), as well as myogenic commitment gene desmin (DES) (Capetanaki et al., 1997) together with all genes necessary for vascular smooth muscle contraction ("KEGG PATHWAY: Vascular smooth muscle contraction-*Homo sapiens* (human)," n.d.) were analyzed in detail. Changes in gene expression between MPCs and iSMCs derived thereof were compared to those between MSCs and iSMCs derived thereof. Considering a log 2 FC of 1 or more and a log 2 FC of −1 or less as an up- and downregulation, respectively, 20.33 percent of the 123 tested genes were up- and only 3.25 percent downregulated during MPCs to MPCs-iSMCs differentiation, suggesting a differentiation towards a smooth muscle cell phenotype. Upregulated genes of the KEGG cluster or known smooth muscle marker genes in MPC-iSMCs compared to MPCs were PPP1R14A, KCNMB1, PLCB4, ACTG2, ITPR1, ADCY6, CALCRL, KCNMA1, GNA13, CNN1, ADCY2, KCNMB4, GUCY1A3, ARAF, ITGA1, PPP1R12A, MAPK1, CALD1, KCNMB2, PRKACB, ARHGEF11, PPP1R12C, ITPR2, PLCB1 and SMTN (FIG. 12).

Considering a log 2 FC of 1 or more and a log 2 FC of −1 or less as an up- and downregulation, respectively, 12.20 percent of the 123 tested genes were up- and only 3.25 percent downregulated during MSCs to MSC-iSMCs differentiation, suggesting a differentiation towards a smooth muscle cell phenotype. Upregulated genes of the KEGG cluster or known smooth muscle marker genes in MSC-iSMCs compared to MSCs were ACTA2, ACTG2, CALD1, GNAQ, ITPR1, MAPK1, MYL9, KCNMA1, PLCB4, PPP1R14A, PRKCE, CNN1, TPM1, TAGLN and ITGA1 (FIG. 12). The findings that gene expression of ITGA1 encoding for CD49a and SMTN encoding for smoothelin proteins were found upregulated in MPCs-iSMCs, supports our findings of increased percent CD49a positive cells and smoothelin positive cells in MPCs-iSMCs compared to MPCs, thus confirming smooth muscle marker expression of MPCs-iSMCs. The finding that gene expression of ITGA1 encoding for CD49a was found upregulated in MSCs-iSMCs, supports our findings of increased percent CD49a positive cells in MSCs-iSMCs compared to MSCs, thus confirming smooth muscle marker expression of MPCs-iSMCs.

Figure 4:
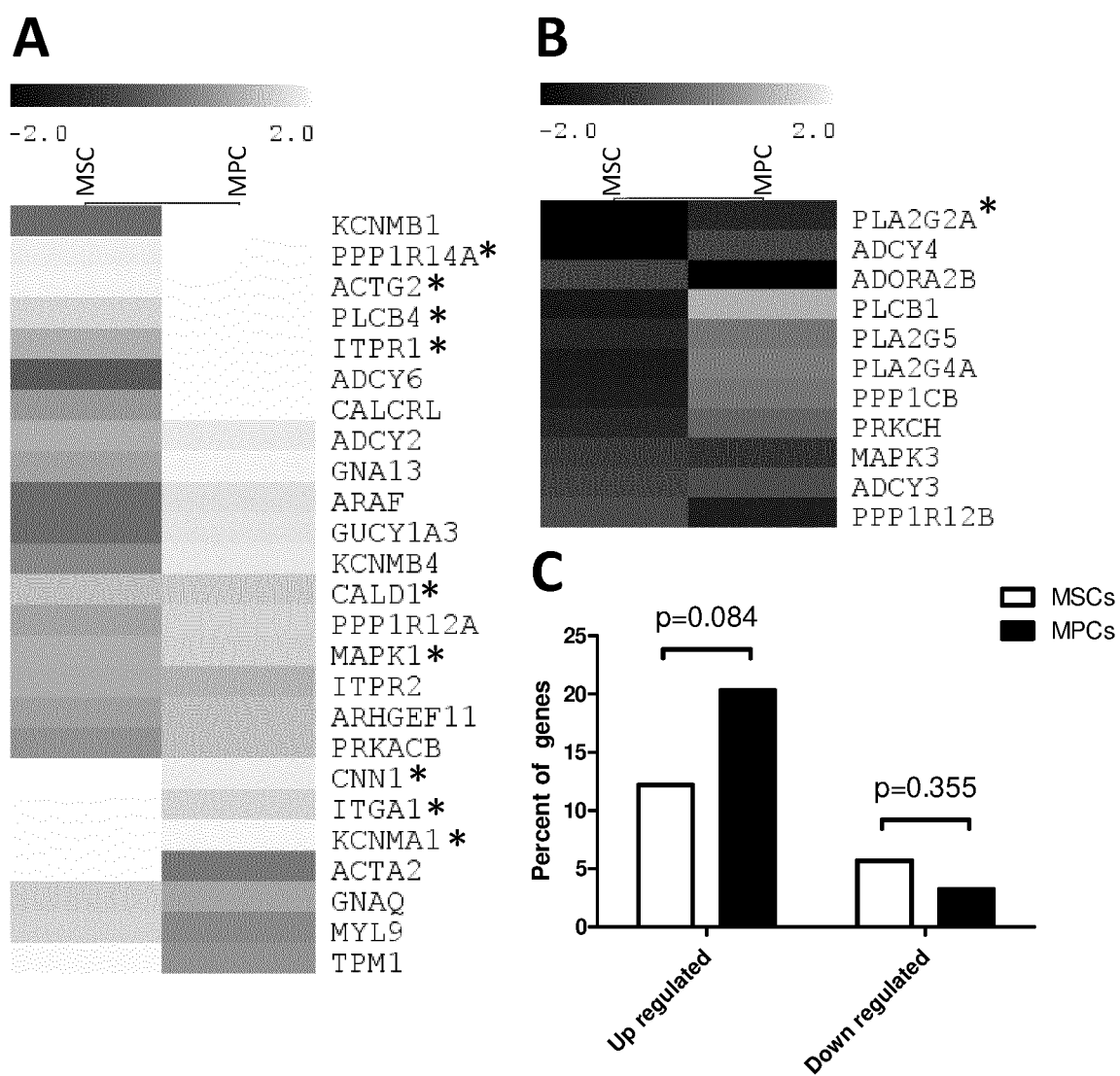

Although, CD146 (MCAM) surface protein expression was upregulated in MPCs-iSMCs, MCAM gene expression was not found to be upregulated in the microarray experiments, suggesting a post-transcriptional regulation of CD146 expression. Further, k-means cluster analysis of log 2 FC changed gene expressions in MPCs and MSCs during differentiation to MPCs-iSMCs and MSCs-iSMCs led to the identification of similarly up- (FIG. 4A) and down regulated (FIG. 4B) genes between MPCs and MSCs when iSMCs were isolated thereof respectively. Whereas PP1R14A, ACTG2, PLCB4, ITPR1, MAPK1, CNN1, ITGA1 and KCNMA1 were upregulated in both, MPCs and MSCs, PLA2G2A was downregulated in both cell types. Overall, 75.61 percent of tested genes are similarly up-, down-, or neither of both regulated within MPCs and MSCs upon differentiation to iSMCs. Although more upregulated genes and less downregulated genes were found in MPCs (20.33% up- and 3.25% downregulated) than MSCs (12.20% up- and 5.69% downregulated), no significant difference in percent up- or downregulated genes was found between MPCs and MSCs (FIG. 4C).

Example 7—Fusion Competency

Fusion competency of MPCs and iSMCs according to Examples 1 and 2 respectively was assessed according to their fusion index (FI). In order to determine the fusion index (FI), cells induced for skeletal muscle differentiation in Example 3, were washed twice with PBS and fixed with 4% PFA for 10 minutes. Next, cells were washed three times with PBS and stained by 2 µg/mL Hoechst33342 solution for 20 minutes. For each sample at least three fields were captured during immunofluorescence imaging and overlaid with phase-contrast images to allow easy detection of nuclei and cell boundaries. Fusion index was calculated for each captured field of vision by dividing the number of nuclei within tubes with the total number of nuclei per field following calculation of the mean for all analyzed fields. Only cells that have at least 3 nuclei were considered as myotubes. For statistical analysis at least 3 populations derived from different patients were analyzed for each group.

Figure 5:
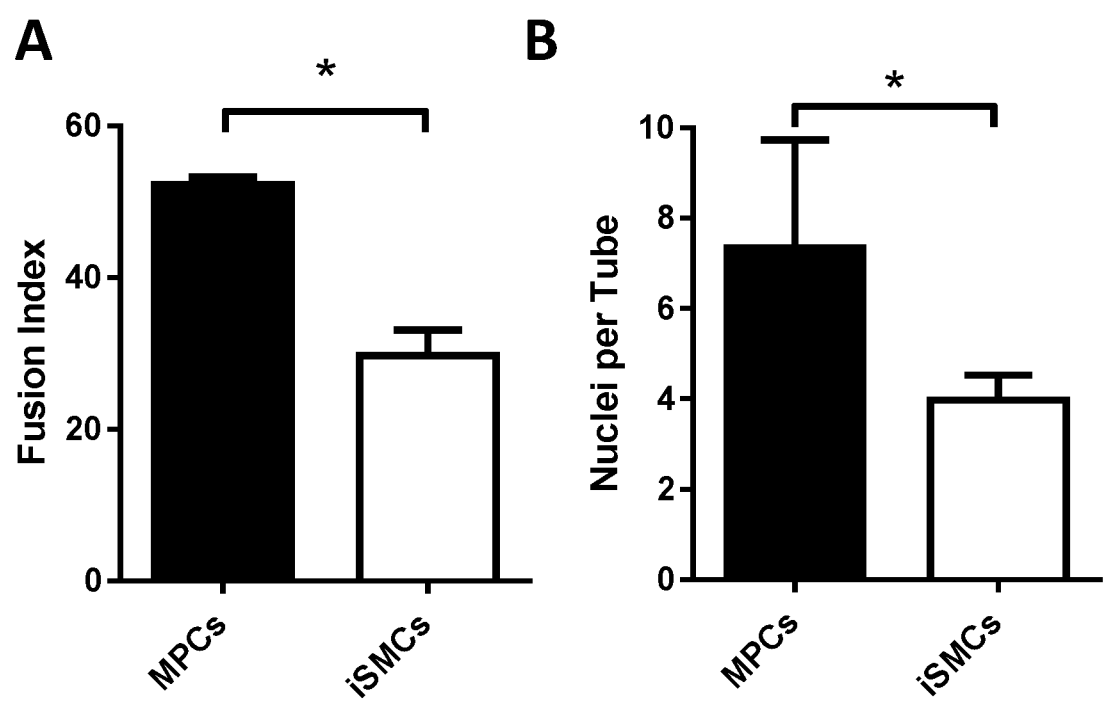

Quantification of the FI demonstrated that significantly more MPCs underwent skeletal myogenesis compared to iSMCs isolated thereof in Example 2, suggesting a decrease in skeletal myogenic potential of MPCs upon isolation of iSMCs from MPCs. (FIG. 5A). Further, tubes formed by iSMCs contained significantly fewer nuclei than tubes formed by MPCs (FIG. 5B). Taken together, MPCs appear fusion-competent, whereas iSMCs derived thereof are considered non-fusion competent.

Example 8—Electrophysiology

Patch-clamp analysis was performed on MPCs and iSMCs obtained according to Examples 1 and 2 respectively, according to a previously published protocol (Park et al., 2013), with slight experiment specific adaptions. Procedures were conducted as follows. Electrophysiological recording was performed in a whole cell configuration using an Axopatch 200A patch clamp amplifier (Axon Instruments, Foster City). Patch pipettes with resistances of 1 to 4 MΩ were made from borosilicate glass (GC150E-7.5, Clark Electromedical Instruments, UK) and filled with pipette solution. All data were digitized using a DIGIDATA 1200 interface (Axon Instruments, Foster City), smoothed by means of a four-pole Bessel filter and saved to disc. Current traces were sampled at 10 kHz and filtered at 2 kHz. The pClamp software package (Version 10.0 Axon Instruments, Inc.) was used for data acquisition. Microcal Origin 7.0 was used for analysis. If not otherwise mentioned, reagents were obtained from Sigma-Aldrich. Inward current of voltage-dependent Cav channels was evoked by applying 500-ms depolarizing pulses from a holding potential of −50 to 50 mV. Superimposed current traces of Kv channels were evoked by step depolarizing pulses between −80 and 60 mV in steps of 20 mV from a holding potential of 80 mV in MPCs, MPCs-iSMCs and hBd-SMCs.

Cells obtained by Example 2 were found neither to exhibit voltage sensitive inward nor outward currents of voltage dependent calcium or voltage dependent potassium channels, respectively. In the contrary, iSMCs derived from MPCs in Example 2 showed both, voltage sensitive inward and outward currents, as also found in hBd-SMCs (FIG. 6). Summarizing, the isolation of iSMCs by incubation with TGFb1 and Heparin results in functional maturation.

Example 9—Collagen Gel Lattice Contraction

In order to measure the contractility of MSCs and MPCs obtained according to Example 1 as well as iSMCs derived thereof by Example 2 were seeded in collagen gel lattice and reduction of percent gel size was quantified. In detail, culture media from sub-confluent cells in standard cell culture vessels were removed and cells were washed twice with 1×PBS. Next, cells were covered with trypsin and incubated for 5 minutes at 37° C. Afterwards, cells were detached by tapping against the walls of the culture vessel and resuspended following addition of DMEM/Ham's F12 basal medium. Then, cells were centrifuged at 400*g for 10 minutes.

Supernatant was removed and cell pellet resuspended in DMEM/Ham's F12 to obtain $6*10^5$ cells per ml. For each gel, 400 µl of cell suspension was mixed with 200 µl collagen solution from bovine skin (Thermo-Fisher Scientific, MA, USA). Next, 3 µl 0.1M NaOH was added followed by immediate resuspension and transfer of 500 µl of the mixture into a well of a 24-well plate (NUNC, Thermo-Fisher Scientific, MA, USA). The 24-well plate was then incubated for 30 minutes at 37° C. to allow gel formation. Afterwards each gel was covered with 500 µl DMEM/Ham's F12 and released from the bottom of the 24 well plate to float on the surface by using a sterile pipette tip. Finally, the gels were incubated at 37° C., 5% $CO_2$ for 24 hours to allow gel contraction by included cells. To quantify gel contraction, stereomicroscopic pictures were taken and the area of the gel was calculated by applying FIJI (image J) software.

MPCs and MSCs isolated according to step (a) of the present invention (Example 1) were found to be non-contractile in collagen gel lattice contraction assay. In contrast, iSMCs isolated according to step (b) of the present invention (Example 2) from MPCs and MSCs did show significantly higher contractility than cells originating from (MPCs, MSCs). In summary, SMDCs transdifferentiated to iSMCs and isolated according to step (b) (Example 2) were found to be contractile compared to cells isolated in step (a) (Example 1; FIG. 7).

Example 10—Smooth Muscle Regeneration Using iSMCs

To test the potential of iSMCs obtained according to Example 2 in terms of smooth regeneration, iSMCs derived from murine MPCs (obtained according to Example 1) were injected into the pyloric sphincter of adult female SHO-Prkdc$^{scid}$Hr$^{hr}$ mice. For this, mice were first anesthetized by applying 100 mg/kg Ketamin; 10 mg/kg Xylazin and 3 mg/kg Acepromazin intraperitoneally. Eye protecting cream was applied during the procedure. Cryopreserved cells were freshly thawed, washed once with 1×PBS and centrifuged at 400*g for 10 minutes followed by resuspending the cells in 1×PBS to reach a final concentration of 40 000 000 cells/ml. Meanwhile the mice that receive cells were placed on a heating plate to maintain body temperature at 37° C. 25 µl of the cell suspension (containing 1 000 000 cells) was then mixed with 5 µl FluoSpheres® polystyrene beads, 15 µm, yellow-green or blue (Thermo-Fisher Scientific, MA, USA), necessary to track the location of the injection after surgery. For iSMCs injection into the pyloric sphincter, a median laparotomy was performed followed by localization of the pyloric sphincter region and application of 30 µl cell-fluosphere mixture using a 28G needle attached to a 1 ml syringe. The peritoneum and muscle-skin layer was closed separately by consecutive stitching with 6-0 ethicon PDS plus absorbable monofilaments. Postoperatively 200 mg Novalgin (Metamizol®) per kilogram bodyweight was applied subcutaneously for three days. 12 weeks after cell injection, mice were sacrificed by cervical dislocation to obtain and image pyloric sphincter muscles.

Imaging of fresh isolated pyloric sphincter regions was performed with an IVIS Spectrum (PerkinElmer, MA, USA) by using Living Image® software version 4.5.2 (PerkinElmer, MA, USA) according to manufacturer's instructions. In short, pyloric sphincters of injected and control SHO-mice were placed on a glass petri dish and placed within the IVIS system. Fluorescence pictures at a height of 2 cm with automated exposure times for corresponding absorption and emission wavelengths of TdTomato and yellow Fluosphere beads were taken. Post hoc, signal intensities were adjusted in order to get rid of background signals by comparing with sphincter explants from control mice.

For histological analysis animals were deeply anesthetized with isoflurane and sacrificed by cervical dislocation. Tissue of interest was immediately dissected and cryo-fixed by plunging into liquid nitrogen cooled 2-methylbutane. Tissue was cut at 15 µm on a Leica 1950 Cryostat and slices were collected on Superfrost plus slides and kept at –20° C. until further processing. For immunohistological analysis sections were fixed with 4% PFA and washed with PBS containing 0.1% Tween-20 (Sigma-Aldrich). Blocking and antibody dilution were performed using a PBS solution containing 1% bovine serum albumin fraction (Sigma-Aldrich), 0.2% fish skin gelatin (Sigma-Aldrich) and 0.1% Tween-20 (Sigma-Aldrich). Primary antibodies against tdTomato (Sicgen) or aSMA (Thermo Scientific, MA, USA) were diluted 1:100 in blocking media following incubation was performed over night at 4° C. Secondary antibodies (Thermo scientific) were diluted 1:500 and applied at room temperature for 4 hours. Nuclei were stained with DAPI diluted to 0.5 µg/ml working concentration (Sigma-Aldrich). Slices were subsequently mounted using Prolong Gold Antifade (Life Technologies). Fluorescence images were acquired using a LSM 710 confocal microscope and ZEN 2011 Black Software (Carl Zeiss).

Figure 8:
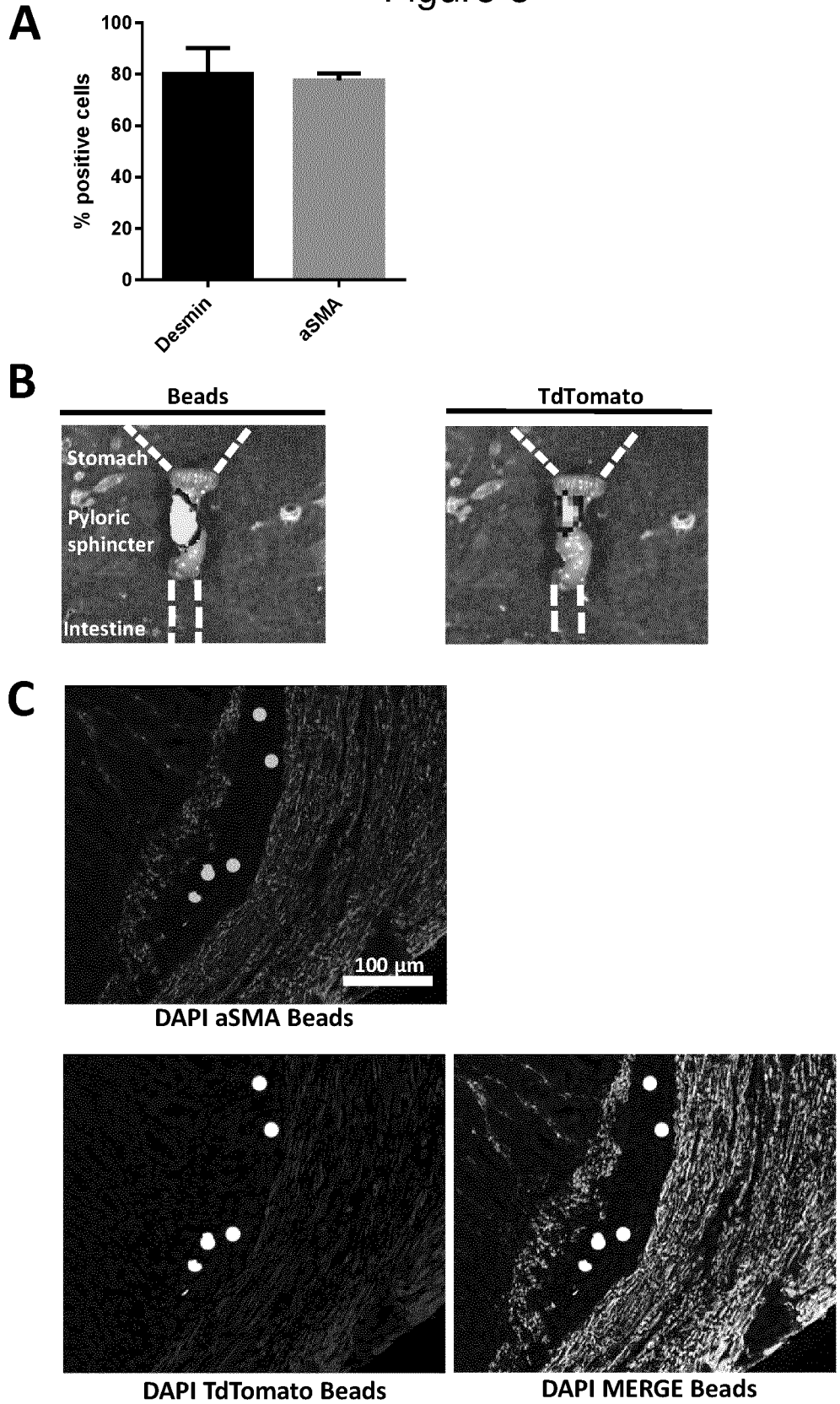

The inventors found that iSMCs isolated according to Example 2 from TdTomato reporter protein expressing MPCs obtained according to Example 1 was detectable and co-localized with co-injected fluorescent beads at the site of the pyloric sphincter 12 weeks post implantation, suggesting the engraftment of iSMCs at the site of injection. Histological examination followed by fluorescence immunostaining for TdTomato and aSMA suggested that TdTomato positive iSMCs cells were found within the pyloric sphincter circular muscle as well as muscularis mucosa nearby co-injected fluorescent beads (FIG. 8). TdTomato positive iSMCs cells located within the smooth muscle layer of the pyloric sphincter also expressed aSMA protein, suggesting not only the engraftment into the smooth muscle tissue but also conserved phenotypic characteristics of smooth muscle cells after engraftment necessary for smooth muscle regeneration (FIG. 8).

Example 11—Tissue Engineering Smooth Muscles

Figure 9:
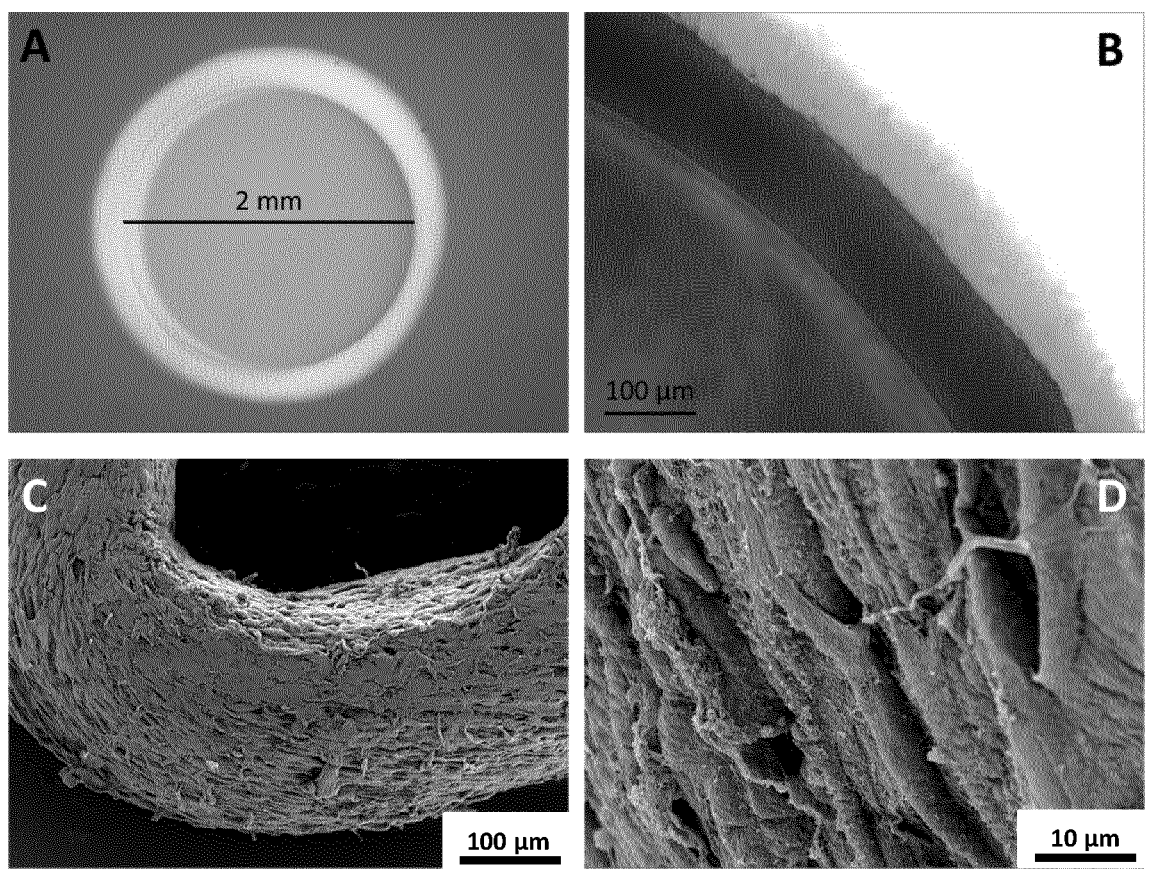

To test the suitability of cells obtained by the methods herein for use in tissue engineering, 3D cell cultivation was performed. A method allowing for the production of ring shaped sphincter like structures already known in the art (Gwyther et al., 2011) was employed using cells obtained according to Example 1 or 2. To produce culture vessels for 3D cultivation, a template with ring shaped carvings (inner diameter 4 mm; outer diameter 10 mm) was made of stainless steel in order to produce an autoclave-able PDMS negative template. Next, a 2% (w/v) agarose solution was prepared by weighing in 5 g low gelling agarose (Sigma-Aldrich, MA, USA) in a Schott® flask filled up to 250 ml with Ham's F10 basal medium. Then, both the PDMS template and agarose solution was autoclaved at 121° C. for 20 minutes. Afterwards, The PDMS template was filled with the agarose solution under sterile conditions followed by incubation at room temperature for 1 hour to let the agarose solidify. In a next step, the solidified agarose was released from the PDMS template, cubes each containing one ring shaped template were cut out of the agarose and transferred to a 6-well plate filled with 2 ml Ham's F10 basal medium followed by storage at 37° C. until further use. For 3D cultivation, cells obtained in Example 1 were centrifuged at 400*g for 10 minutes and the cell pellet was resuspended in culture medium to reach a concentration of $5 \times 10^6$ cells/ml. Next, 200 µl of the cell suspension was added into the agarose template followed by incubation at 37° C. for 48 hours without further disturbances to allow ring formation of the cells. After the incubation time, medium outside the template within the 6-well plate was discarded and the 6-well plate was carefully filled with 5 ml medium as used in Example 1 to produce 3D cultured MPCs or MSCs or any of the latter as used in Example 2 to produce iSMCs 3D cultures. Cells were cultivated for 6 days to allow maturation at 37° C., 5% $CO_2$ until analysis. After 6 days of cultivation, cells were analyzed by standard light microscopy, cryo-sectioning followed by immunostaining (Example 12) or H&E staining, scanning electron microcopy or semi/ultra-thin sectioning followed by toluidine blue staining or transmission electron microcopy. MPCs derived according to Example 1 that were transdifferentiated towards iSMCs as described in Example 2, did form ring shaped sphincters employing the above described methods based on Gwyther et al., 2014 (FIG. 9).

Example 12—Cryo-Sectioning and Immunostaining

For histological analysis of ring shaped 3D cultures (bioengineered sphincters) obtained according to Example 11, rings were carefully removed from the agarose template and using a sterile spoon, washed by transferring into a Eppendorf tube filled with 1×PBS and then fixed and permeabilized by submerging in –20° C. pre-cooled MetOH for 5 minutes. Next, rings were washed by diluting MetOH three times with 1×PBS following removal of half of the solution. Bioengineered sphincters were cryo-fixed by plunging into liquid nitrogen cooled 2-methylbutane. Specimen were cut at 15 µm on a CM1950 Cryostat (Leica, Germany) and slices were collected on Superfrost plus slides (Thermo-Fisher Scientific, MA, USA) and kept at −20° C. until further processing. Blocking and antibody dilution was performed using a PBS solution containing 1% bovine serum albumin fraction (Sigma-Aldrich Co. LLC, MO, USA), 0.2% fish skin gelatin (Sigma-Aldrich Co. LLC, MO, USA) and 0.1% Tween-20 (Sigma-Aldrich Co. LLC, MO, USA). Primary antibody aSMA (Thermo-Fisher Scientific, MA, USA) was diluted 1:100 in blocking media followed by overnight incubation at 4° C. Secondary antibodies (Thermo-Fisher Scientific, MA, USA) were diluted 1:500 and applied at room temperature for 4 hours. Nuclei were stained with DAPI diluted to 0.5 µg/ml working concentration (Sigma-Aldrich Co. LLC, MO, USA) and actin filaments were stained by incubation with Phalloidin (Thermo-Fisher Scientific, MA USA) diluted 1:100 in PBS for 20 minutes at room temperature. Slices were subsequently mounted using Prolong Gold Antifade (Thermo-Fisher Scientific, MA, USA). Fluorescence images were acquired using a Nikon Eclipse TE2000-U inverted Micro scope.

Figure 10:
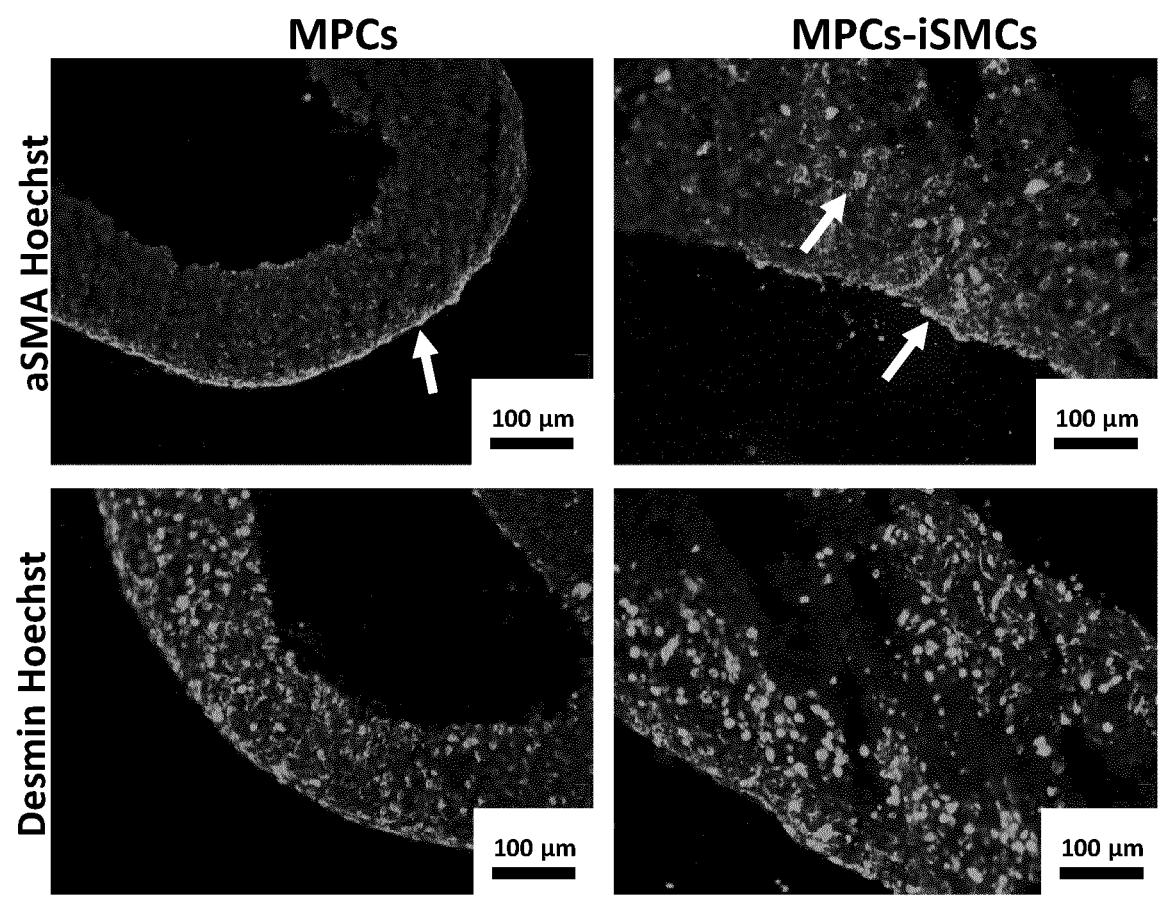
FIG. 10 illustrates the expression of contractile proteins in SMDCs and iSMCs derived tissue rings by immunofluorescence. Immunofluorescence staining of general myogenic (Desmin) and smooth muscle myogenic (aSMA) markers together with nuclei counterstaining (Hoechst) performed on cryo-sections of tissue rings obtained from 3D cultivation of MPCs as well as iSMCs derived thereof.

It was found that cells within the tissue rings obtained according to Example 10 were positive for alpha smooth muscle actin and desmin (FIG. 10). Whereas, within MPCs derived tissue rings aSMA was expressed especially by cells at the outer layer of the ring, within iSMCs containing tissue rings aSMA expressing cells were distributed over the total ring. In detail, more cells within rings that formed from MPCs differentiated to iSMCs during 3D cultivation according to combination of Example 2 and 10 were found to express aSMA than cells within rings that formed from MPCs (FIG. 10). In contrast, desmin was expressed all over the tissue rings in both MPCs and iSMCs derived tissue rings (FIG. 10).

Example 13—Scanning Electron Microcopy

Scanning electron microscopy was performed at the department of histology and embryology of the Medical University of Innsbruck thankfully under the help of Angelika Flörl and Kristian Pfaller. For the analysis of 3D cultured cells obtained by Example 1 and 2 (as described in section 3.2.26) by scanning electron microscopy, rings were released from agarose templates, washed once in a 1.5 ml Eppendorf® tube with 1×PBS and then fixed with pre-cooled (−20° C.) MetOH, followed by 1 hour post-fixation in 1% osmium tetroxide, dehydration with EtOH and critical point drying in a Bal-Tec CPD 030 critical point dryer (Balzers, Lichtenstein). Specimen were mounted with conductive carbon cement Leit-C after Gocke (Plano GmbH, Wetzlar, Germany) on aluminum stubs sputter-coated with 15 nm Au/Pd (Balzers) and examined on a Gemini 982 scanning electron microscope (Carl Zeiss). MPCs obtained according to Example 1 and transdifferentiated towards iSMCs as described in Example 2 during 3D cultivation (Example 2) appeared elongated and as an integral part of the tissue ring on the surface of the tissue rings that had formed in Example 10 (FIG. 9). Cells appeared intact on the surface of the ring and potentially viable (FIG. 9).

Example 14—Transmission Electron Microscopy

Transmission electron microscopy was performed on tissue rings obtained according to Example 10. Therefore rings were released form agarose template and transferred to a 1.5 ml Eppendorf tube filled with 1×PBS for washing. Next, samples were transferred to a fresh Eppendorf® tube filled with 2.5% Glutaraldehyde in 0.1 M Phosphate buffer (pH 7.3) for fixation and storage (4° C.). After at least 24h of fixation, rings were washed twice with phosphate buffer and then fixed in 1% $OsO_4$ for 45 minutes. Afterwards, rings were washed three times with distilled water, each 15 minutes. Then, rings were de-liquidized in increasing EtOH concentrations (70, 80, 90, 100%), each 30 minutes and then incubated twice in fresh 100% Aceton for each 20 minutes. Next, specimens were embedded in 2:1 Aceton-Epon mixtures for 150 minutes followed by incubation in 1:2 Aceton-Epon mixture overnight. Finally, rings were incubated in pure Epon rotating on a rotator for 24 hours with a change of Epon after 8 hours. For polymerization of Epon, rings were incubated at 60° C. for 24 hours. Epon embedded specimen were trimmed using an Ultratrim (Reichert) and ultra-thin sections, were obtained using an Ultracut S (Reichert). Ultrathin sections were viewed at 80 kV with a CM120 TEM (from Philips/FEI) equipped with a MORADA CCD-camera (from Olympus/SIS).

Figure 11:
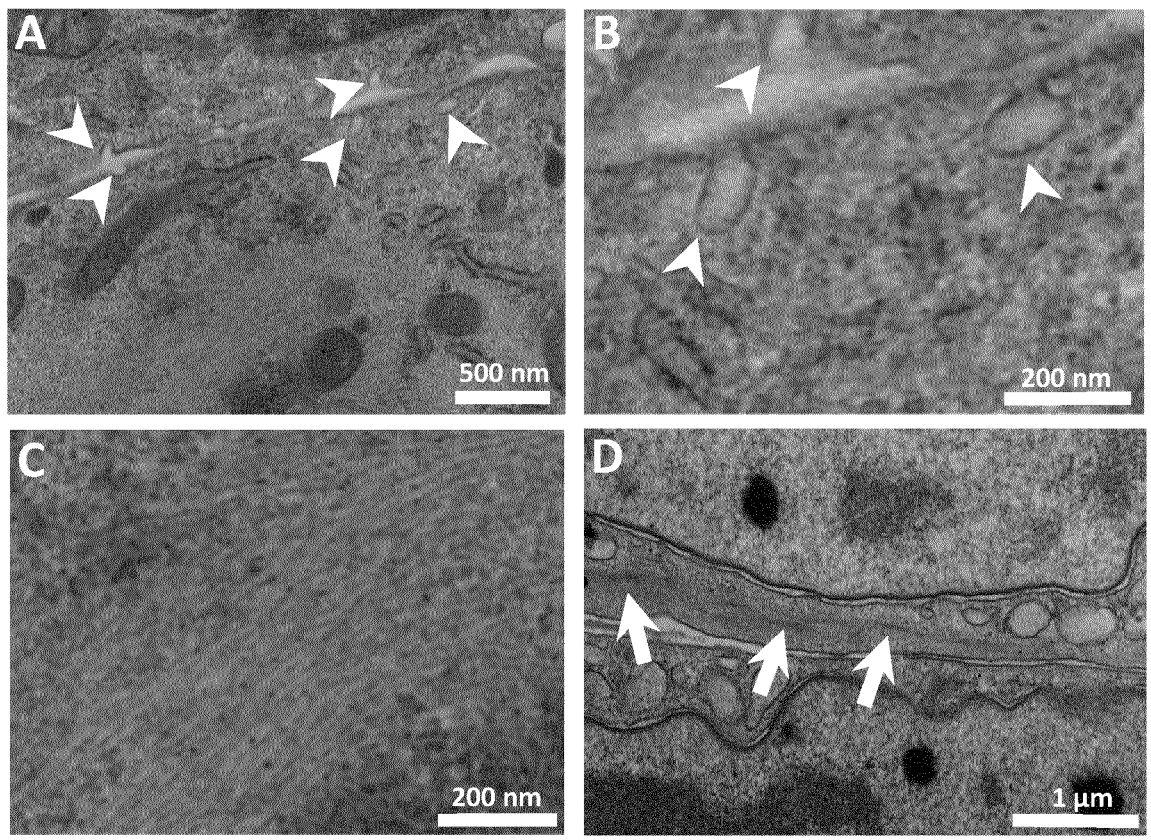
FIG. 11 illustrates transmission electron microscopic images of tissue rings.

Transmission electron microscopy of tissue rings obtained according to Example 10 revealed that cells have formed calveolae near their plasma membrane (FIGS. 11 A and B). Further it was found that cells within the tissue rings had a dominant actin structure (Figure C), which at some parts of the cells formed dense packaged structures like dense bodies (Figure D).

Example 15—Surface Marker Expression of Murine MPC-iSMCs

To determine surface marker expression of murine MPC-iSMCs, flow cytometry was performed on a Guava easyCyte 6HT 2L flow cytometer (Merck Millipore, Darmstadt, Germany). Briefly, murine MPC-iSMCs obtained by Example 1 were used for antibody staining procedures of a commercially available mouse cell surface marker screening panel (BD biosciences, NJ, USA). Therefore, cells were suspended in growth medium at a concentration of $1.25*10^6$ cells per ml and aliquots of 100 µl cell suspension was mixed with all primary antibodies in 96-well plates according to manufacturers' instructions. The mixture was incubated for 30 minutes at 4° C. followed by addition of 100 µl growth medium to each well, centrifugation of the plates for 5 minutes at 300*g, removal of supernatant, addition of 200 µl growth medium to each well, another centrifugation, removal of supernatant and resuspension of cells in 100 µl biotinylated secondary antibodies (prepared according to manufacturer's instructions). Cells were incubated again for 30 minutes at 4° C. followed by addition of 100 µl growth medium to each well, centrifugation of the plates for 5 minutes at 300*g, removal of supernatant, addition of 200 µl growth medium to each well, another centrifugation, removal of supernatant and resuspension of cells in 100 µl Alexa647 conjugated streptavidin (prepared according to manufacturer's instructions). Cells were incubated again for 30 minutes at 4° C. followed by addition of 100 µl growth medium to each well, centrifugation of the plates for 5 minutes at 300*g, removal of supernatant, addition of 200 µl growth medium to each well, another centrifugation, removal of supernatant and resuspension of cells in 200 µl Ham's F10 supplemented with 10% FCS. Finally, cell events were acquired with Guava InCyte™ v.2.3 software. Histograms and dot-plots were generated with a minimum of 5000 events at a sample flow rate of 1.8 µL/mL. Positive staining was obtained by comparison with Isotype control set as at least 95% negative or comparison to control (negative) cells. Murine iSMCs of Example 3 were found to be CD49e− (FIG. 13).

Example 16—Analysis of Intracellular Marker by Flow Cytometry

Briefly, MPCs and MPC-iSMCs obtained by Example 1 were harvested by covering adherent cells with 1× trypsin at 37° C. for 5 minutes, following detachment cells were centrifuged at 400*g. Cells were counted and aliquoted to achieve 50,000 cells/reaction, which then were centrifuged at 400×g followed by resuspension in BD Cytofix/Cytoperm Fixation and Permeabilization Solution (BD Biosciences, Pharmingen™) and incubated at 4° C. for 20 min. Afterwards, cells were washed with BD Perm/Wash Buffer (diluted 1:10 in aqua dest) (BD Biosciences, Pharmingen™) and centrifuged. Cells were then resuspended in 1×PBS and incubated with IgG Isotype Control-Alexa488 (Bioss Antibodies Inc., MA, USA) or anti-Pax-7-Alexa488 (Bioss Antibodies Inc., MA, USA) for 1 h at 4° C. in the dark. Subsequently, the cells were centrifuged, washed with BD Perm/Wash buffer (diluted 1:10 in aqua dest) and after a final centrifugation step resuspended in 1×PBS. Cell events were acquired by employing Guava InCyte™ v.2.3 software. Histograms were generated with a minimum of 3000 events with a sample flow rate of 1.8 µl/ml. The percentage of positive cells was obtained by comparison with isotype control set as 99% negative.

Example 17—Analysis of Enzyme Activities

Acetylcholinesterase Activity Measurement
Reagent and Standard Preparation:

American Public Health Association (APHA) Phosphate buffer, pH 7.2 (Sigma-Aldrich Co. LLC, Germany) was prepared according to manufacturer's instructions. In summary, 17 g of powdered mixture (monopotassium phosphate, 22.66 g/L and sodium carbonate 7.78 g/L) was added into 400 mL distilled water. After adding 0.5 mL Triton X-100, the mixture was dissolved on a magnetic stirrer for 30 minutes at room temperature. The final volume was made up to 500 mL in a measuring cylinder and was used without further dilution. The buffer was stored at 4° C. until use. Ellman's reagent (5,5'-dithiobis-2-nitrobenzoic acid, DTNB, 0.5 mM) was prepared freshly for each AChE assay by weighing out 2 mg in 1.5 mL Eppendorf tube. It was dissolved in 1 mL of phosphate buffer (pH 7.2 with 0.1% triton X-100) by vortexing it for 1-2 minutes. The final volume was made up to 10 mL in a 15 mL falcon tube with phosphate buffer (pH 7.2 with 0.1% triton X-100) and was stored at 4° C. until use. Acetylcholine thioiodide (ATI, 5.76 mM) was prepared freshly for each AChE assay by weighing out 2 mg in 1.5 mL eppendorf tube. It was dissolved in 1.2 mL of distil water by vortexing for 1-2 minutes and then stored at 4° C. until use.

AChE standard dilutions were prepared in phosphate buffer (pH 7.2 with 0.1% triton X-100) and were immediately used. A ready to use 50 U/mL AChE stock (from Electrophorus electricus) was purchased from AAT Bioquest® Inc., Sunnyvale, Calif., USA. It was diluted to prepare 1000 mU/mL of AChE according to manufacturer's instructions, which was further diluted in a 1:2 ratio to obtain 8 different dilutions ranging from 4-500 mU/mL.

Colorimetric Measurement:

In order to measure the activity of AChE, cells obtained by cultivation in skeletal muscle differentiation medium according to Example 3 were treated as following: Differentiation medium was carefully removed from 24-well plate with the immediate addition of 300 µL 0.5 mM DTNB solution (prepared in phosphate buffer, pH 7.2 with 0.1% triton X-100). After 2 minutes of incubation at room temperature in dark, 50 µL of 5.76 mM ATI (prepared in distil water) was added. The reaction contents were incubated for 60 minutes at 30° C. in dark followed by the OD measurement at 412 nm on an Anthos Zenyth 340rt microplate reader (Biochrom Ltd., Cambridge, UK).

For AChE enzyme-standard analysis: Dilutions of AChE enzyme-standard (AAT® Bioquest, Sunnyvale, USA) ranging from 500 to 4 mU/ml were prepared as described above and 200 µL of each AChE standard enzyme dilution was mixed with 300 µL of 0.5 mM DTNB and 50 µL of 5.76 mM ATI. OD of the mixture was measured for 60 minutes in a 24-well plate.

Calculation of AChE $mU_{rel}$/Mg-Protein:

AChE $mU_{rel}$ was calculated based on OD412 values obtained from 60 min colorimetric measurement of cells by extrapolation of linear standard curves derived from AChE standard measurements (OD at 412 nm after 7 or 8 minutes). AChE $mU_{rel}$/mg protein values were then calculated by dividing AChE $mU_{rel}$ with mg of total protein (calculated according to Example 19) of corresponding cells cultivated in skeletal muscle differentiation medium.

Creatine Kinase Activity Measurement

In order to measure the activity of AChE, cells obtained by cultivation in skeletal muscle differentiation medium according to Example 3 were treated as following: The medium from cells grown on a 24-well plate was gently removed and cells were washed with 1 ml of Tryrode's salt solution (Sigma-Aldrich Co. LLC, MO, USA). Immediately afterwards, 70 µl lysis buffer was added directly onto the cells. Lysis buffer was prepared by adding 10 µl of Triton-X-100 to 10 ml of $dH_2O$ (LC-MS-Ultrachromasol, Fluka). After 5 minutes incubation at 4° C. in dark, 400 µl of CK-NAC (Thermo Scientific, MA, USA), previously dissolved by adding 10 ml $dH_2O$, was added. The reaction was analyzed in an Anthos Zenith 340rt microplate reader (Biochrom Ltd., Cambridge, UK) set to 30° C., by OD absorbance measurement at 340 nm. If not otherwise mentioned, OD340 nm values taken 21 minutes after addition of CK-NAC, were used for subsequent analysis. CK activity in $mU_{rel}$ was calculated according to manufacturer's instructions and if not otherwise mentioned normalized by dividing it by mg total protein of corresponding cells.

Whereas MPCs of Example 3 analyzed for ACHE and CK activity according to this example were found to be AChE+ and CK+, iSMCs of the present invention (Example 3) were found to be AChE- and CK-(FIG. 14).

Example 18—Comparison of Cells According to the Present Invention with Cells Known in the Art Thurner et al. 2018 described the isolation of SMDC, which were characterized either to be CD56+ or CD56-. In order to compare the cells described by Thurner et al. 2018 with cells of the present invention, the authors of referred study were contacted and asked for provision of samples. The authors agreed to hand out cells isolated according to Thurner et al. 2018, and thus these cells could be tested according to Examples 3, 4, 5, 7, 8, 9, 16 and 17 of the present invention and were compared to MPCs, MSCs, MPC-iSMCs and MSC-iSMCs isolated by Example 1. The results are shown in FIG. 15.

Frudinger et al. 2018 described the isolation of SMDC, which were characterized to be CD56+. In order to compare the cells described by Frudinger et al. 2018 with cells of the present invention, the authors of referred study were contacted and asked for provision of samples. The authors agreed to hand out cells isolated according to Frudinger et al. 2018, and thus these cells were tested according to Examples 3, 4, 5, 7, 8, 9, 16 and 17 of the present invention and compared to MPCs, MSCs, MPC-iSMCs and MSC-iSMCs isolated by Example 1. The results are shown in FIG. 15.

Example 19—Protein Quantification

Cells obtained by cultivation in skeletal muscle differentiation medium according to Example 3 were analyzed for total protein quantification according to Thurner et al. 2018. Therefore, adherent cells were first washed twice with PBS, subsequently covered with PBST (0.1% Triton X-100) and then incubated for 10 minutes at room temperature. Next, the lysate was resuspended and transferred to an Eppendorf® tube, shortly vortexed and then centrifuged for 4 minutes at 1200*g. Finally, the clear supernatant was transferred into a fresh Eppendorf tube and the protein concentration was determined using the Pierce BCA Protein Assay Kit (Thermo Scientific, MA, USA) according to the manufacturer's instructions by measuring the OD at 540 nm with an Anthos Zenyth 340rt microplate reader (Biochrom Ltd., Cambridge, UK).

REFERENCES

Abrahamsson, H. (2007). *Gut,* 56(6), 877-883.
Al-Ali, S., Blyth, P., Beatty, S., Duang, A., Parry, B., & Bissett, I. P. (2009). *Journal of Anatomy,* 215(2), 212-220.
Bajpai, V. K., Mistriotis, P., Loh, Y.-H., Daley, G. Q., & Andreadis, S. T. (2012). *Cardiovascular Research,* 96(3), 391-400.
Belkin, V. M., Belkin, A. M., & Koteliansky, V. E. (1990). *The Journal of Cell Biology,* 111(5 Pt 1), 2159-2170.
Bohl, J. L., Zakhem, E., & Bitar, K. N. (2017). *Stem Cells Translational Medicine,* 6(9), 1795-1802.
Capelli, C. C., Chancellor, M. B., Huard, J., & Qu, Z. (2002). WO2001078754A3
Capetanaki, Y., Milner, D. J., & Weitzer, G. (1997). *Cell Structure and Function,* 22(1), 103-116.
Chancellor, M. B., Huard, J., Capelli, C. C., & Qu, Z. (2001). WO2001078754 A2
Dash, B. C., Levi, K., Schwan, J., Luo, J., Bartulos, O., Wu, H., Qiu, C., Yi, T., Ren, Y., Campbell, S., Rolle, M. W., & Qyang, Y. (2016). *Stem Cell Reports,* 7(1), 19-28.
Dominici, M., Le Blanc, K., Mueller, I., Slaper-Cortenbach, I., Marini, F., Krause, D., Deans, R., Keating, A., Prockop, D., & Horwitz, E. (2006). *Cytotherapy,* 8(4), 315-317.
Espagnolle, N., Guilloton, F., Deschaseaux, F., Gadelorge, M., Sensébé, L., & Bourin, P. (2014). *Journal of Cellular and Molecular Medicine,* 18(1), 104-114.
Frudinger, A., Kölle, D., Schwaiger, W., Pfeifer, J., Paede, J., & Halligan, S. (2010). *Gut,* 59(1), 55-61.
Frudinger, A., Pfeifer, J., Paede, J., Kolovetsiou-Kreiner, V., Marksteiner, R., & Halligan, S. (2015). *Colorectal Disease: The Official Journal of the Association of Coloproctology of Great Britain and Ireland,* 17(9), 794-801.
Frudinger, Andrea, Marksteiner, R., Pfeifer, J., Margreiter, E., Paede, J., & Thurner, M. (2018). *Stem Cell Research & Therapy,* 9(1), 233.
Goode, P. S., Burgio, K. L., Halli, A. D., Jones, R. W., Richter, H. E., Redden, D. T., Baker, P. S., & Allman, R. M. (2005). *Journal of the American Geriatrics Society,* 53(4), 629-635.
Huard, J., Yokoyama, T., Pruchnic, R., Qu, Z., Li, Y., Lee, J. Y., Somogyi, G. T., de Groat, W. C., & Chancellor, M. B. (2002). *Gene Therapy,* 9(23), 1617-1626.
Iivanainen, A., Sainio, K., Sariola, H., & Tryggvason, K. (1995). *FEBS Letters,* 365(2-3), 183-188.
Jung, Y., Bauer, G., & Nolta, J. A. (2012). *Stem Cells* (Dayton, Ohio), 30(1), 42-47.
Krauss, R. S., Chihara, D., & Romer, A. I. (2016). *Skeletal Muscle,* 6.
Lecourt, S., Marolleau, J.-P., Fromigué, O., Vauchez, K., Andriamanalijaona, R., Ternaux, B., Lacassagne, M.-N., Robert, I., Boumédiene, K., Chéreau, F., Marie, P., Larghéro, J., Fiszman, M., & Vilquin, J.-T. (2010). *Experimental Cell Research,* 316(15), 2513-2526.
Li, Y., Wen, Y., Wang, Z., Wei, Y., Wani, P., Green, M., Swaminathan, G., Ramamurthi, A., Pera, R. R., & Chen, B. (2016). *STEM CELLS Translational Medicine,* 5(12), 1719-
Lu, S.-H., Lin, A. T. L., Chen, K.-K., Chiang, H. S., & Chang, L. S. (2011). *Journal of Cellular and Molecular Medicine,* 15(3), 587-592.
Marolleau, J.-P., Vauchez, K., & Vilquin, J.-T. (2010). EP2206774A1.
McHugh, K. M. (1995). *Developmental Dynamics: An Official Publication of the American Association of Anatomists,* 204(3), 278-290.
Meyer, I., & Richter, H. E. (2015). *Women's Health* (London, England), 11(2), 225-238.
Mimura, T., Kaminishi, M., & Kamm, M. A. (2004). *Digestive Surgery,* 21(3), 235-241.
Niessen, P., Rensen, S., Deursen, J. van, Man, J. D., Laet, A. D., Vanderwinden, J.-M., Wedel, T., Baker, D., Doevendans, P., Hofker, M., Gijbels, M., & Eys, G. van. (2005). *Gastroenterology,* 129(5), 1592-1601.
Park, W. S., Heo, S. C., Jeon, E. S., Hong, D. H., Son, Y. K., Ko, J.-H., Kim, H. K., Lee, S. Y., Kim, J. H., & Han, J. (2013). *American Journal of Physiology. Cell Physiology,* 305(4), C377-91.
Popescu, L. M., Gherghiceanu, M., Mandache, E., & Cretoiu, D. (2006). *Journal of Cellular and Molecular Medicine,* 10(4), 960-990.
Quander, C. R., Morris, M. C., Melson, J., Bienias, J. L., & Evans, D. A. (2005). *The American Journal of Gastroenterology,* 100(4), 905-909.
Qu-Petersen, Z., Deasy, B., Jankowski, R., Ikezawa, M., Cummins, J., Pruchnic, R., Mytinger, J., Cao, B., Gates, C., Wernig, A., & Huard, J. (2002). *The Journal of Cell Biology,* 157(5), 851-864.
Ramkumar, D., & Schulze, K. S. (2005). *Neurogastroenterology and Motility: The Official Journal of the European Gastrointestinal Motility Society,* 17 Suppl 1, 22-30.
Rao, S. S. C. (2004). *Gastroenterology,* 126(1 Suppl 1), S14-22.
Rochlin, K., Yu, S., Roy, S., & Baylies, M. K. (2010). *Developmental Biology,* 341(1), 66-83.
Romanska, H. M., Bishop, A. E., Moscoso, G., Walsh, F. S., Spitz, L., Brereton, R. J., & Polak, J. M. (1996). *Journal of Pediatric Gastroenterology and Nutrition,* 22(4), 351-358.
Sanders, K. M. (2008). *Neurogastroenterology and Motility: The Official Journal of the European Gastrointestinal Motility Society,* 20 Suppl 1, 39-53.
Sandison, M., & McCarron, J. (2015). *The FASEB Journal,* 29(1 Supplement), 418.8.
Skuk, D., Goulet, M., & Tremblay, J. P. (2014). *Cell Transplantation,* 23(1), 13-25.
Thurner, M., Asim, F., Garczarczyk-Asim, D., Janke, K., Deutsch, M., Margreiter, E., Troppmair, J., & Marksteiner, R. (2018). *PLOS ONE,* 13(3), e0194561.

Vaizey, C. J., Kamm, M. A., & Bartram, C. I. (1997). *Lancet* (London, England), 349(9052), 612-615.

van de Rijn, M., Hendrickson, M. R., & Rouse, R. V. (1994). *Human Pathology*, 25(8), 766-771.

van Eys, G. J., Niessen, P. M., & Rensen, S. S. (2007). *Trends in Cardiovascular Medicine*, 17(1), 26-30.

Wang, G., Jacquet, L., Karamariti, E., & Xu, Q. (2015). *The Journal of Physiology*, 593(14), 3013-3030.

Wang, J. Y., & Abbas, M. A. (2013). *The Permanente Journal*, 17(3), 65-73.

Wang, J., Zohar, R., & McCulloch, C. A. (2006). *Experimental Cell Research*, 312(3), 205-214.

Wang, Y., Han, Z., Song, Y., & Han, Z. C. (2012). *Stem Cells International*, 2012.

Webb, R. C. (2003). *Advances in Physiology Education*, 27(4), 201-206.

Wörl, J., Breuer, C., & Neuhuber, W. L. (2009). *Developmental Dynamics*, 238(4), 864-874.

Yin, H., Price, F., & Rudnicki, M. A. (2013). *Physiological Reviews*, 93(1), 23-67.

The invention claimed is:

1. An in vitro or ex vivo method for obtaining induced smooth muscle cells (iSMCs), the method comprising the steps of:
   (a) obtaining skeletal muscle-derived cells from a subject;
   (b) transdifferentiating skeletal muscle-derived cells by cultivating the cells in a medium containing TGF-beta and heparin to obtain iSMCs,
   wherein the skeletal muscle-derived cells are myogenic progenitor cells (MPCs) characterized by the positive expression of CD56 and desmin, and the negative expression of CD3.

2. The method according to claim 1, wherein the iSMCs obtained in step (b) are non-fusion competent and/or characterized by the positive expression of aSMA, CD49a, and CD146.

3. The method according to claim 1, wherein the iSMCs obtained from MPCs in step (b) are characterized by the positive expression of aSMA, CD49a, desmin, CD56, and CD146, and the negative expression of CD3.

4. The method according to claim 1, wherein after step (a) a step (a1) is conducted comprising proliferating the skeletal muscle-derived cells.

5. The method according to claim 1, wherein step (b) is conducted for one to six days.

6. The method according to claim 1, wherein TGF-beta in step (b) of claim 1 is:
   (i) TGFb1, TGFb2 and/or TGFb3, or
   (11) TGFb1 and/or TGFb3, or
   iii) TGFb1.

7. The method of claim 1, wherein the TGF-beta is TGFb1.

* * * * *

UNITED STATES PATENT AND TRADEMARK OFFICE
CERTIFICATE OF CORRECTION

PATENT NO. : 12,312,600 B2
APPLICATION NO. : 17/441690
DATED : May 27, 2025
INVENTOR(S) : Marco Thurner et al.

Page 1 of 1

It is certified that error appears in the above-identified patent and that said Letters Patent is hereby corrected as shown below:

In the Claims

Column 36, Line 4, please delete "expression of CD3." and insert --expression of CD34.-- therefor.

Column 36, Line 12, please delete "expression of CD3." and insert --expression of CD34.-- therefor.

Signed and Sealed this
Twenty-sixth Day of August, 2025

Coke Morgan Stewart
*Acting Director of the United States Patent and Trademark Office*